United States Patent
Yoshimura

(10) Patent No.: US 9,074,190 B2
(45) Date of Patent: Jul. 7, 2015

(54) CELL DIFFERENTIATION OF ADIPOSE-DERIVED PRECURSOR CELLS

(75) Inventor: Kotaro Yoshimura, Tokyo (JP)

(73) Assignee: BIOMASTER, INC., Tokyo (JP)

( * ) Notice: Subject to any disclaimer, the term of this patent is extended or adjusted under 35 U.S.C. 154(b) by 2583 days.

(21) Appl. No.: 10/574,435

(22) PCT Filed: Mar. 10, 2004

(86) PCT No.: PCT/JP2004/003143
§ 371 (c)(1),
(2), (4) Date: Aug. 18, 2008

(87) PCT Pub. No.: WO2005/035738
PCT Pub. Date: Apr. 21, 2005

(65) Prior Publication Data
US 2008/0317718 A1    Dec. 25, 2008

(30) Foreign Application Priority Data

Oct. 7, 2003 (JP) ................................ 2003-348897
Feb. 16, 2004 (JP) ................................ 2004-039096

(51) Int. Cl.
*C12N 5/0775* (2010.01)
*A61K 35/12* (2015.01)

(52) U.S. Cl.
CPC ............... *C12N 5/0667* (2013.01); *A61K 35/12* (2013.01); *C12N 2502/1305* (2013.01); *C12N 2502/1311* (2013.01); *C12N 2502/28* (2013.01)

(58) Field of Classification Search
CPC ........... A61K 2300/00; A61K 31/4025; A61K 31/4015; A61K 31/381; A61K 31/45; A61K 35/35; A61K 31/728; A61K 8/981; A61K 8/4913; A61K 2800/91; A61K 8/4926; A61K 8/4986; A61K 8/49; A61K 31/4412; A61K 38/1767; A61K 31/192; C12N 5/0667; C12N 5/069; C12N 2506/1384; C12N 5/0651; C12N 2500/02; C12N 2501/15; C12N 2501/155; C12N 2506/28; C12N 5/0663; C12N 5/0668; C12N 5/0696
See application file for complete search history.

(56) References Cited

U.S. PATENT DOCUMENTS

| | | | | |
|---|---|---|---|---|
| 5,092,883 | A * | 3/1992 | Eppley et al. ................. | 424/422 |
| 5,681,561 | A * | 10/1997 | Hirshowitz et al. .......... | 424/93.7 |
| 5,858,390 | A * | 1/1999 | Boss, Jr. ........................ | 424/426 |
| 6,777,231 | B1 * | 8/2004 | Katz et al. ..................... | 435/325 |
| 7,887,795 | B2 * | 2/2011 | Fraser et al. ................. | 424/93.7 |
| 2003/0082152 | A1 | 5/2003 | Hedrick et al. ............ | 424/93.21 |
| 2006/0147430 | A1 * | 7/2006 | Sayre et al. .................. | 424/93.7 |

FOREIGN PATENT DOCUMENTS

WO    WO99/64566 A     12/1999
WO    01/62901 A2      8/2001

OTHER PUBLICATIONS

Gimble, Jeffrey M et al. "Differentiation Potential of Adipose Derived Adult Stem (ADAS) Cells" *Current Topics in Developmental Biology*, 58:137-60, 2003.
Lee, James A. et al. "Biological Alchemy: Engineering Bone and Fat From Fat-Derived Stem Cells," *Annals of Plastic Surgery*, 50(6):610-617, Jun. 2003.
Van, Robin L. R., et al., "Complete Differentiation In Vivo of Implanted Cultured Adipocyte Precursors from Adult Rats," *Cell and Tissue Research*, 225(3): 557-566, Aug. 1982.
International Search Report dated Aug. 13, 2004 in Application No. PCT/JP2004/003143.
Written Opinion dated Apr. 7, 2006 in Application No. PCT/JP2004/003143.
International Preliminary Report on Patentablity dated Apr. 10, 2006 in Application No. PCT/JP2004/003143.

* cited by examiner

*Primary Examiner* — Blaine Lankford
(74) *Attorney, Agent, or Firm* — Snell & Wilmer L.L.P.

(57) ABSTRACT

The present invention provides a simple method for controlled differentiation of adipose-derived precursor cells. A method is provided for preparing a differentiated cell. The method comprises A) obtaining a mixture by mixing a) an adipose-derived precursor cell and b) a differentiated cell corresponding to a desired site; and B) culturing the mixture under sufficient conditions which allow the adipose-derived precursor cell to differentiate. The present invention also provides a composition for cell implantation comprising a) an adipose-derived precursor cell and b) a differentiated cell corresponding to a desired site.

8 Claims, 5 Drawing Sheets

CELL DIFFERENTIATION OF ADIPOSE-DERIVED PRECURSOR CELLS

CROSS-REFERENCE TO RELATED APPLICATIONS

This application is a U.S. national stage filing under 35 U.S.C. §371 of PCT/JP2004/003143, filed Mar. 10, 2004, which claims priority to and the benefit of Japanese Application No. 2003-348897, filed Oct. 7, 2003, and Japanese Application No. 2004-039096, filed Feb. 16, 2004. All of the aforementioned applications are incorporated herein by reference.

TECHNICAL FIELD

The present invention relates to the field of cell differentiation. More particularly, the present invention relates to the differentiation of adipose-derived precursor cells and an implantation therapy and a cosmetic therapy using the same.

BACKGROUND ART

Regenerative medicine, mainly utilizing stem cells, has considerably progressed in recent years. Various tissue stem cells, which had not been considered to be present, were discovered and identified in various tissues. Thus, attention has been focused on disease therapy using (regenerative therapy).

However, regenerative therapy has not yet reached a point where it is conventionally applied to numerous patients suffering from organ or tissue dysfunction. To date, a very limited number of such patients have been treated by organ transplantation or use of an auxiliary medical system or apparatus. These therapies are problematic in shortage of donors, rejection, infection, durability, and the like. Particularly, the donor shortage raises serious problems. In the case of bone marrow transplantation, bone marrow and umbilical cord blood banks have gradually become more widely used home and abroad, though it is still difficult to provide a limited amount of samples to a number of patients. Therefore, there is an increasing demand for therapies using stem cells and regenerative medicine using the same in order to overcome the above-described problems. Use of foreign tissue for organ implantation (e.g., heart, blood vessels, etc.) is hindered mainly by immune rejection responses. Changes occurring in allogenic grafts (or allografts) and xenografts are well known.

After gastrulation, a fertilized egg is divided into three germ layers, i.e., endoderm, mesoderm, and ectoderm. Cells derived from the ectoderm are mainly present in brain, including neural stem cells and the like. Cells derived from the mesoderm are mainly present in bone marrow, including blood vessel stem cells, hematopoietic stem cells, mesenchymal stem cells, and the like. Cells derived from the endoderm are mainly present in organs, including liver stem cells, pancreatic stem cells, and the like.

Mesenchymal cells, such as adipocytes, bones, ligaments, cardiac muscles, and the like, have an important function of forming the shape or skeleton of the body. Therefore, there is an increasing expectation for the application of groups or tissues of such cell store generative medicine and implantation medicine. Particularly, it has been reported that bone marrow mesenchymal stem cells can be differentiated into mesodermal organs, and such stem cells have attracted attention mainly in the field of regenerative medicine. However, differentiation of such cells requires special conditions where a special medium containing a differentiation inducing agent (e.g., dexamethasone, etc) is required (Nakatsuji, ed., "Kansaibo Kuron Kenkyu Purotokoru [Stem cell/Clone Research Protocol]", Yodosha (2001)).

Mesenchymal stem cells are a type of tissue stem cells. Mesenchymal stem cells naturally occur only in a small amount (one ten thousandth of all cells in the bone marrow of human neonates, thereafter reducing quickly, and one two millionth of all cells in elderly persons). It is therefore difficult to isolate mesenchymal stem cells. As it has been reported that mesenchymal stem cells are differentiated into germ layers other than mesoderm, the range of applications is becoming widespread. However, conditions for such differentiation are more specific than those which are described above. The known surface antigens of mesenchymal stem cells are CD105(+), CD73(+), CD29(+), CD44(+), CD14(−), CD34(−), and CD45(−).

On the other hand, it has been found that fat contains stem cells (WO00/53795; WO03/022988; WO01/62901; Zuk, P. A., et al., Tissue Engineering, Vol. 7, 211-228, 2001; Zuk, P. A., et al., Molecular Biology of the Cell, Vol. 13, 4279-4295, 2002). Fat supplies a larger amount of stem cells than other tissues (e.g., bone marrow, etc.) and the density of stem cells seems to be higher. Therefore, fat has attracted attention. However, methods for treating stem cells are not fully understood.

For bone marrow-derived stem cells, various methods for inducing the cells to differentiate to target cells in vitro are known (WO96/39035, WO97/41208, WO99/64565, WO97/40137, and WO00/06701). It has been demonstrated that in vitro induction of differentiation can be performed with a method similar to that for bone marrow-derived mesenchymal stem cells. However, there has been no such report for adipose-derived precursor cells. In addition, there has been no report known for in vivo induction of differentiation. The destiny of a tissue stem cell is determined to some degree by its origin. It is believed that even if stem cells are treated under the same conditions, the level of differentiation differs from tissue stem cell to tissue stem cell. Attempts have been made to utilize adipocytes in medicine (Japanese Laid-Open Publication No. 2001-103963, Japanese Laid-Open Publication No. 2001-103965, and WO99/28444), but there has been no report for clinical trials of adipose-derived precursor cells.

Alternatively, a cosmetic therapy has been practiced, in which fat is removed and transplanted. In this method, however, it is difficult to obtain a desired shape and a satisfactory level of affinity. It cannot be said that the desired result of cosmetic surgery is obtained. Therefore, there is a demand for a surgical method for obtaining a desired cosmetic effect and a material or medicament for use in such a method.

Thus, there is an increasing demand for a simple method for controlled differentiation of adipose-derived precursor cells in the art. An object of the present invention is to meet such a demand. An other object of the present invention is to provide a clinical method for obtaining a desired cosmetic effect and a material or medicament for use in such a method.

DISCLOSURE OF THE INVENTION

The present invention was completed by the present inventors who have diligently studied the above-described problems, in part based on our unexpected finding that by implanting a mixture of a cell corresponding to a desired site (e.g., an adipocyte for fat, a bone cell for bone, etc.) with an adipose-derived precursor cell or its crude preparation, the precursor cell is differentiated into a desired cell.

Therefore, the present invention provides the following.

1. A method for preparing a differentiated cell, comprising the steps of:
   A) obtaining a mixture by mixing
      a) an adipose-derived precursor cell, and
      b) a differentiated cell corresponding to a desired site; and
   B) culturing the mixture under sufficient conditions which allow the adipose-derived precursor cell to differentiate.
2. A method according to item 1, wherein the differentiated cell is a mesenchymal cell.
3. A method according to item 1, wherein the differentiated cell is selected from the group consisting of adipocytes, bone marrow cells, osteoblasts, chondrocytes, fibroblasts, myofibroblasts, nerve cells, skeletal muscle cells, cardiac muscle cells, vascular endothelial cells, vascular smooth muscle cells, hepatic cells, and renal cells.
4. A method according to item 1, wherein the adipose-derived precursor cell is a cell expressing at least one protein selected from the group consisting of CD13, CD29, CD34, CD36, CD44, CD49d, CD54, CD58, CD69, CD71, CD73, CD90, CD105, CD106, CD151, and SH3.
5. A method according to item 4, wherein the adipose-derived precursor cell is a cell expressing CD13, CD29, CD34, CD36, CD44, CD49d, CD54, CD58, CD69, CD71, CD73, CD90, CD105, CD106, CD151, and SH3.
6. A method according to item 4, wherein the adipose-derived precursor cell is the cell further expressing at least one protein selected from the group consisting of CD31, CD45, CD117, and CD146.
7. A method according to item 1, wherein the adipose-derived precursor cell is a cell not expressing CD56.
8. A method according to item 1, wherein the adipose-derived precursor cell is a cell expressing CD49d but not CD56.
9. A method according to item 1, further comprising providing an agent for promoting differentiation into a differentiated cell.
10. A method according to item 1, wherein the mixture is cultured in a medium containing at least one ingredient selected from the group consisting of adrenocortical steroids, insulin, glucose, indomethacin, isobutyl-methylxanthine (IBMX), ascorbic acid and a derivative thereof, glycerophosphate, estrogen and a derivative thereof, progesterone and a derivative thereof, androgen and a derivative thereof, growth factors, pituitary gland extracts, pineal body extracts, retinoic acid, vitamin D, thyroid hormone, fetal bovine serum, equine serum, human serum, heparin, sodium hydrogen carbonate, HEPES, albumin, transferrin, selenates, linoleic acid, 3-isobutyl-1-methylxanthine, demethylating agent, histone deacetylating agents, activin, cytokine, hexamethylenebisacetamide (HMBA), dimethylacetamide (DMA), dibutyl cAMP (db-cAMP), dimethylsulfoxide (DMSO), iododeoxyuridine (IdU), hyroxyurea (HU), cytosine arabinoside (AraC), mitomycin C (MMC), sodiumbutyrate (NaBu), polybrene, and selenium.
11. A method according to item 1, wherein the abundance ratio of the adipose-derived precursor cell to the differentiated cell corresponding to the desired site is higher than the abundance ratio of a stem cell to the differentiated cell in healthy tissue at the desired site.
12. A method according to item 1, wherein the proportion of the adipose-derived precursor cell in the mixture is higher than the proportion of a stem cell in healthy tissue at the desired site.
13. A method according to item 1, wherein the proportion of the adipose-derived precursor cell in the mixture is about 2 to about 10 times higher than the proportion of a stem cell in healthy tissue at the desired site.
14. A cell mixture, comprising:
   an adipose-derived precursor cell; and
   a differentiated cell corresponding to a desired site.
15. A cell mixture according to item 14, wherein the abundance ratio of the adipose-derived precursor cell to the differentiated cell corresponding to the desired site is higher than the abundance ratio of a stem cell to the differentiated cell in healthy tissue at the desired site.
16. A cell mixture according to item 14, wherein the abundance ratio of the adipose-derived precursor cell to the differentiated cell corresponding to the desired site is about 2 to about 10 times higher than the abundance ratio of a stem cell to the differentiated cell in healthy tissue at the desired site.
17. A cell mixture according to item 14, wherein the abundance ratio of the adipose-derived precursor cell to the differentiated cell corresponding to the desired site is about 2 to about 5 times higher than the abundance ratio of a stem cell to the differentiated cell in healthy tissue at the desired site.
18. A cell mixture according to item 14, wherein the cell mixture is exposed under sufficient conditions which allow the adipose-derived precursor cell to differentiate.
19. A cell mixture according to item 14, wherein the differentiated cell corresponding to the desired site is an adipocyte, and the proportion of the adipose-derived precursor cell in the mixture is higher than the proportion of the adipose-derived precursor cell in fat tissue.
20. A cell mixture according to item 19, wherein the proportion of the adipose-derived precursor cell in the mixture is higher than the proportion of the adipose-derived precursor cell in healthy tissue at the desired site.
21. A cell mixture according to item 19, wherein the proportion of the adipose-derived precursor cell in the mixture is about 2 to about 10 times higher than the proportion of the adipose-derived precursor cell in healthy tissue at the desired site.
22. A cell mixture according to item 19, wherein the adipose-derived precursor cell is derived from suctioned fat.
23. A cell mixture according to item 19, wherein the adipose-derived precursor cell is derived from a liquid portion of an aspirate from liposuction.
24. A composition for cell implantation, comprising:
   a) an adipose-derived precursor cell; and
   b) a differentiated cell corresponding to a desired site.
25. A composition according to item 24, wherein the composition is implanted into the desired site.
26. A composition according to item 24, wherein the differentiated cell is a mesenchymal cell.
27. A composition according to item 24, wherein the differentiated cell is selected from the group consisting of adipocytes, bone marrow cells, osteoblasts, chondrocytes, fibroblasts, myofibroblasts, nerve cells, skeletal muscle cells, cardiac muscle cells, vascular endothelial cells, vascular smooth muscle cells, hepatic cells, and renal cells.
28. A composition according to item 24, wherein the differentiated cell is provided in suctioned fat.
29. A composition according to item 24, wherein the differentiated cell is provided in a liquid portion of an aspirate from liposuction.
30. A composition according to item 24, further comprising at least one ingredient selected from the group consisting of adrenocortical steroids, insulin, glucose, indomethacin, isobutyl-methylxanthine (IBMX), ascorbic acid and a derivative thereof, glycerophosphate, estrogen and a derivative thereof, progesterone and a derivative thereof, androgen and a derivative thereof, growth factors, pituitary gland extracts, pineal body extracts, retinoic acid, vitamin D, thyroid hormone, fetal bovine serum, equine serum, human serum, heparin, sodium hydrogen carbonate, HEPES, albumin, transferrin, selenates, linoleic acid, 3-isobutyl-1-methylxanthine, demethylating agent, histone deacetylating agents, activin, cytokine, hexamethylenebisacetamide (HMBA), dimethylacetamide (DMA), dibutyl cAMP (dbcAMP), dimethylsulfoxide (DMSO), iododeoxyuridine (IdU), hyroxyurea (HU), cytosine arabinoside (AraC), mitomycin C (MMC), sodiumbutyrate (NaBu), polybrene, and selenium.

31. A composition according to item 24, wherein the adipose-derived precursor cell is allogenic to the differentiated cell.
32. A composition according to item 24, wherein the adipose-derived precursor cell is isologous to the differentiated cell.
33. A method for treatment or prevention of a disease, a disorder or an abnormal condition attributed to the deficiency of a differentiated cell, comprising the steps of:
    A) providing a composition comprising:
        a) an adipose-derived precursor cell; and
        b) a differentiated cell corresponding to a desired site; and
    B) administering the composition to a subject.
34. A medicament for treatment or prevention of a disease, a disorder or an abnormal condition attributed to the deficiency of a differentiated cell, comprising:
    a) an adipose-derived precursor cell;
    b) a differentiated cell corresponding to a desired site; and
    c) a pharmaceutically acceptable carrier.
35. Use of a mixture of: a) an adipose-derived precursor cell; and b) a differentiated cell corresponding to a desired site, for preparation of a medicament for treatment or prevention of a disease, a disorder or an abnormal condition attributed to the deficiency of a differentiated cell.
36. A method for treatment or improvement of a cosmetic condition, comprising the steps of:
    A) providing a composition comprising:
        a) an adipose-derived precursor cell; and
        b) a differentiated cell corresponding to a desired site; and
    B) administering the composition to a subject.
37. A method according to item 36, wherein the differentiated cell corresponding to the desired site is an adipocyte.
38. A method according to item 36, wherein the differentiated cell corresponding to the desired site is derived from abdominal fat.
39. A method according to item 36, wherein the cosmetic condition is of chest.
40. A method according to item 36, further comprising obtaining the differentiated cell corresponding to the desired site from fat of the subject.
41. A method according to item 40, the step of obtaining fat is performed by suctioning fat.
42. A method according to item 36, further comprising obtaining the adipose-derived precursor cell from the abdomen of the subject.
43. A method according to item 36, further comprising obtaining the adipose-derived precursor cell from suctioned fat of the subject.
44. A method according to item 43, further comprising obtaining the adipose-derived precursor cell from a liquid portion of an aspirate from liposuction.
45. A medicament for treatment or improvement of a cosmetic condition, comprising:
    a) an adipose-derived precursor cell;
    b) a differentiated cell corresponding to a desired site; and
    c) a pharmaceutically acceptable carrier.
46. A medicament according to item 45, wherein the cosmetic condition is of chest.
47. A medicament according to item 45, wherein the differentiated cell corresponding to the desired site is an adipocyte.
48. A medicament according to item 45, wherein the differentiated cell corresponding to the desired site is an abdominal adipocyte.
49. A medicament according to item 45, wherein the adipose-derived precursor cell is derived from abdominal fat.
50. A medicament according to item 45, wherein the proportion of the adipose-derived precursor cell in the medicament is higher than the proportion of a stem cell in healthy tissue at the desired site.
51. A medicament according to item 45, wherein the pharmaceutically acceptable carrier comprises a cell culture medium or a buffer.
52. Use of a mixture of: a) an adipose-derived precursor cell; and b) a differentiated cell corresponding to a desired site, for preparation of a medicament for treatment or improvement of a cosmetic condition.
53. Use according to item 52, wherein the abundance ratio of the adipose-derived precursor cell to the differentiated cell corresponding to the desired site is higher than the abundance ratio of a stem cell to the differentiated cell in healthy tissue at the desired site.
54. Use according to item 52, wherein the proportion of the adipose-derived precursor cell in the mixture is about 2 to about 10 times higher than the proportion of a stem cell in healthy tissue at the desired site.

According to the present invention, stem cells obtained from fat tissue can be used for regenerative therapy and cosmetic treatment. Further, according to the present invention, blending an adipose-derived precursor cell with a differentiated cell can induce the adipose-derived precursor cell to be differentiated into the desired differentiated cell. Furthermore, according to the present invention, adipose-derived precursor cells induce vascularization, which facilitates implanted differentiated cells and regenerated differentiated cells to be accepted by an implantation site. Substantially no side effects are expected in these treatments, and the supply source is abundant. Therefore, the present invention provides a simple and efficient treatment method for regenerative and cosmetic medicine.

Figure 1:
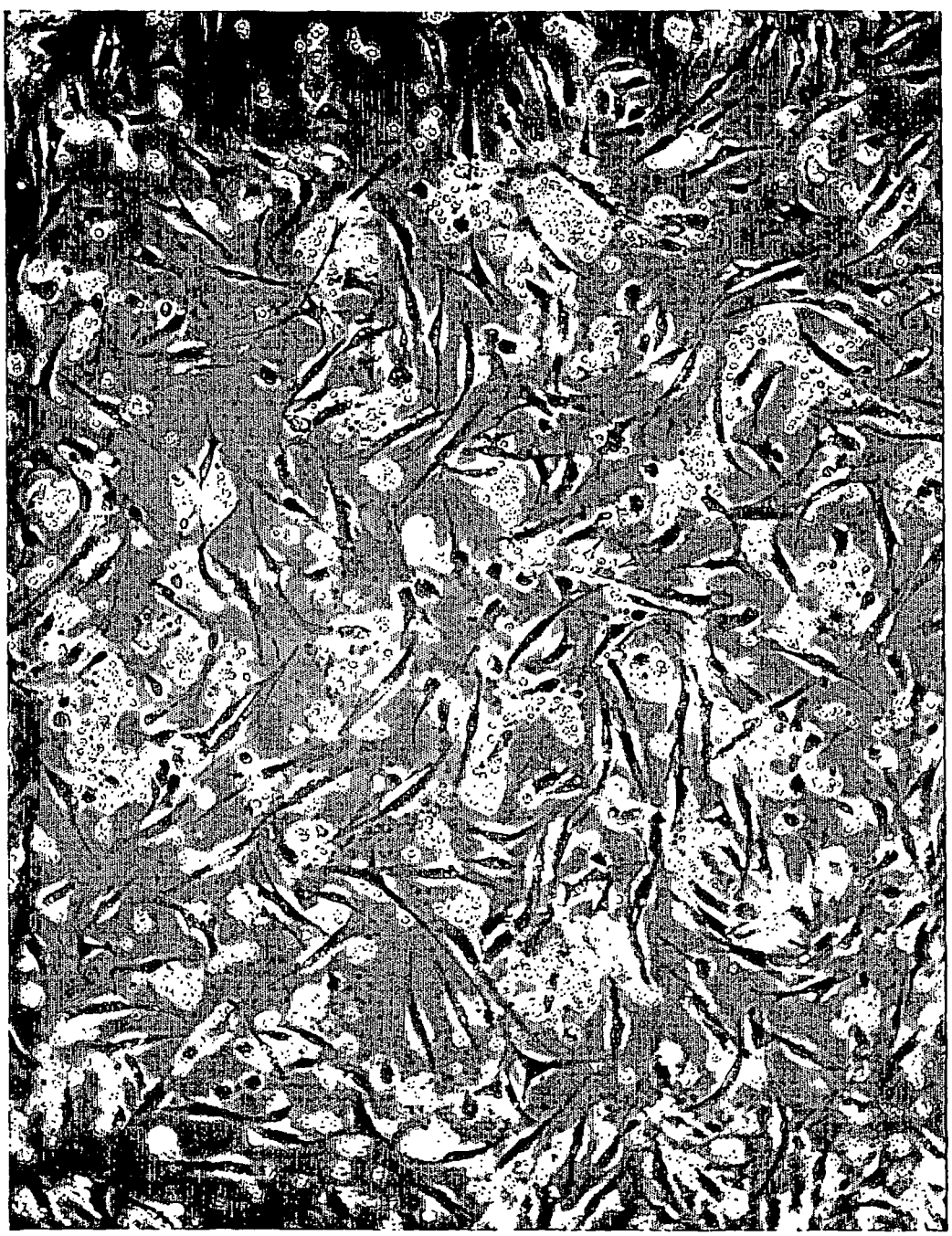
FIG. 1 is a photograph showing stem cells derived from a liquid portion of an aspirate from liposuction, which was prepared according to a method described in Example 2.

These and other advantages of the present invention will be apparent from the drawings and a reading of the detailed description thereof.

BEST MODE FOR CARRYING OUT THE INVENTION

Hereinafter, the present invention will be described. It should be understood throughout the present specification that articles for singular forms (e.g., "a", "an", "the", etc. in English) include plural referents unless the context clearly dictates otherwise. It should be also understood that the terms as used herein have definitions typically used in the art unless otherwise mentioned. If there is contradiction, the present specification (including the definition) takes precedence.

(Definition of Terms)

Terms particularly used herein are defined as follows.

The term "cell" is herein used in its broadest sense in the art, referring to a structural unit of tissue of a multicellular organism, which is capable of self replicating, has genetic information and a mechanism for expressing it, and is surrounded by a membrane structure which isolates the living body from the outside. In the method of the present invention, any cell can be used as a subject. The number of cells used in the present invention can be counted through an optical microscope. When counting using an optical microscope, the number of nuclei is counted. Tissues are sliced into tissue sections, which are then stained with hematoxylin-eosin (HE) to distinguish nuclei derived from extracellular matrices (e.g., elastin or collagen) and cells. These tissue sections are observed under an optical microscope and the number of nuclei in a particular area (e.g., 200 µm×200 µm) can be estimated to be the number of cells. Cells used herein may be either naturally-occurring cells or artificially modified cells (e.g., fusion cells, genetically modified cells, etc.). Examples of cell sources include, but are not limited to, a single-cell culture; the embryo, blood, or somatic tissue (e.g., adipose or fat tissue) of a normally-grown transgenic animal; a cell mixture of cells derived from normally-grown cell lines; and the like. Such a supply source itself can be used as cells.

Fat cells (adipocytes) and their corresponding material used in the present invention may be derived from any organism (e.g., Myxiniformes, Petronyzoniformes, Chondrichthyes, Osteichthyes, Amphibia, Reptilia, Aves, Mammalia, etc.), more preferably mammalian (e.g., Monotremata, Marsupialia, Edentate, Dermoptera, Chiroptera, Carnivora, Insectivora, Proboscidea, Perissodactyla, Artiodactyla, Tubulidentata, Pholidota, Sirenia, Cetacean, Primates, Rodentia, Lagomorpha, etc.) as long as such an organism has adipocytes or cells corresponding thereto. In one embodiment, cells derived from Primates (e.g., chimpanzee, Japanese monkey, human) are used. Most preferably, cells derived from a human are used, but the present invention is not limited thereto.

As used herein, the term "stem cell" refers to a precursor (or progenitor) of a differentiated cell, which has monopotency, multipotency, or totipotency. Stem cells can be differentiated in response to specific stimuli. Typically, stem cells can regenerate an injured tissue. Stem cells used herein may be, but are not limited to, embryonic stem (ES) cells, tissue stem cells (also called tissular stem cell, tissue-specific stem cell, or somatic stem cell), or other precursor cells. A stem cell may be an artificially produced cell (e.g., fusion cells, reprogrammed cells, or the like used herein) as long as it can have the above-described abilities. Embryonic stem cells are pluripotent stem cells derived from early embryos. An embryonic stem cell was first established in 1981, which has been applied to production of knockout mice since 1989. In 1998, a human embryonic stem cell was established, which is currently becoming available for regenerative medicine. Tissue stem cells have a relatively limited level of differentiation unlike embryonic stem cells. Tissue stem cells are present in tissues and have an undifferentiated intracellular structure. Tissue stem cells have a higher nucleus/cytoplasm ratio and have few intracellular organelles. Most tissue stem cells have pluripotency, a long cell cycle, and proliferative ability beyond the life of the individual. As used herein, stem cells may be preferably embryonic stem cells, though tissue stem cells may also be employed depending on the circumstance.

As used herein, the term "stem cell" also refers to a tissue containing a certain amount of stem cells or precursor cells. Therefore, stem cells collected from fat tissue by collagen treatment (e.g., adipose-derived precursor cells used in the examples below, etc.) can be used without limitation.

Tissue stem cells are separated into categories of sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

As used herein, the term "mesenchymal stem cell" refers to a stem cell found in mesenchyme. The term "mesenchymal stem cell" may be herein abbreviated as "MSC". Mesenchyme refers to a population of free cells which are in the asterodal shape or have irregular projections and bridge gaps between epithelial tissues, and which are recognized in each stage of development of multicellular animals. Mesenchyme also refers to tissue formed with intracellular cement associated with the cells. Mesenchymal stem cells have proliferative ability and the ability to differentiate into bone cells, chondrocytes, muscle cells, stroma cells, tendon cells, and adipocytes. Mesenchymal stem cells are employed in order to culture or grow bone marrow cells or the like collected from patients, or differentiate them into chondrocytes or osteoblasts. Mesenchymal stem cells are also employed as reconstructive material, such as alveolar bones; bones, cartilages or joints for arthropathy or the like; and the like. There is a large demand for mesenchymal stem cells. Also, mesenchymal stem cells can be differentiated into blood cells and lymphoid cells. Therefore, there is an increasing demand for mesenchymal stem cells.

As used herein, the term "adipose-derived precursor cell" refers to a stem cell and also other precursor cells, such as stem cells from peripheral blood or vascular-stromal cells (preadipocytes), obtained from liposuction. Adipose-derived precursor cells mean any multipotent or monopotent precursor cell populations derived from the adipose tissue or obtained from liposuction procedure. They include adipose-derived vascular-stromal cells (=preadipocytes, adipose-derived interstitial cells), adipose-derived stem cells, fat stem cells, endothelial progenitor cells, hematopoietic stem cells, and soon. Some techniques for isolating such a stem cell are known as described in, for example, Nakatsuji, ed., "Kansaibo Kuron Kenkyu Purotokoru [Stem cell/Clone Research Protocol]", Yodosha (2001); WO00/53795; WO03/022988; and WO01/62901. These documents are herein incorporated by reference in their relevant portions. As used herein, the term "adipose-derived precursor cell" refers to all fat tissue-derived stem cells including fat tissue-derived stem cells obtained by these known isolation methods. As used herein, the term "precursor cell" includes not only multipotent undifferentiated cells but also monopotent undifferentiated cells. As used herein, the term "stem cell" encompasses precursor cells. The term "PLA (processed lipoaspirate cell)" refers to a precursor cell which is obtained from the fat proportion (lipoaspirate) of an aspirate from liposuction. Precursor cells derived from a liquid portion of an aspirate from liposuction may be referred to as "liquid-aspirate cells". Adipose-derived precursor cells include PLA cells and liquid-aspirate cells.

As used herein, the term "somatic cell" refers to any cell other than a germ cell, such as an egg, a sperm, or the like, which does not transfer its DNA to the next generation. Typically, somatic cells have limited or no pluripotency. Somatic cells used herein may be naturally-occurring or genetically modified as long as they can achieve the intended treatment.

As used herein, the term "differentiated cell" refers to a cell having a specialized function and form (e.g., muscle cells, neurons, etc.). Unlike stem cells, differentiated cells have no or little pluripotency. Examples of differentiated cells include epidermic cells, pancreatic parenchymal cells, pancreatic duct cells, hepatic cells, blood cells, cardiac muscle cells, skeletal muscle cells, osteoblasts, skeletal myoblasts, neurons, vascular endothelial cells, pigment cells, smooth muscle cells, adipocytes, bone cells, chondrocytes, and the like. Differentiated cells used in the present invention may be in the form of a group or tissue.

The origin of a stem cell is categorized into the ectoderm, endoderm, or mesoderm. Stem cells of ectodermal origin are mostly present in the brain, including neural stem cells. Stem cells of endodermal origin are mostly present in bone marrow, including blood vessel stem cells and differentiated cells thereof, hematopoietic stem cells and differentiated cells thereof, mesenchymal stem cells and differentiated cells thereof, and the like. Stem cells of mesoderm origin are mostly present in organs, including liver stem cells and differentiated cells thereof, pancreatic stem cells and differentiated cells thereof, and the like. Somatic cells may be herein derived from any germ layer. Preferably, mesenchymal somatic cells may be used.

As used herein, the term "adipocyte" refers to a cell which is located between tissues or forms fat tissue as areolar tissue or a group along capillary blood vessels, and which contains a large amount of lipid. Fat cells include a yellow adipocyte and a brown adipocyte. They may be equivalently used herein. Fat within cells can be easily detected with Sudan III or osmium tetroxide.

As used herein, the term "desired site" refers to any portion of a subject for which treatment is desired. In the present invention, it will be understood that such a desired site may be selected from any organ or tissue of a subject.

As used herein, the term "tissue" refers to an aggregate of cells having substantially the same function and/or form in a multicellular organism. "Tissue" is typically an aggregate of cells of the same origin, but may be an aggregate of cells of different origins as long as the cells have the same function and/or form. Therefore, when stem cells of the present invention are used to regenerate tissue, the tissue may be composed of an aggregate of cells of two or more different origins. Typically, a tissue constitutes a part of an organ. Animal tissues are separated into epithelial tissue, connective tissue, muscular tissue, nervous tissue, and the like, on a morphological, functional, or developmental basis. Plant tissues are roughly separated into meristematic tissue and permanent tissue according to the developmental stage of the cells constituting the tissue. Alternatively, tissues may be separated into single tissues and composite tissues according to the type of cells constituting the tissue. Thus, tissues are separated into various categories. Any tissue may be herein intended as a target to be treated.

Any organ may be targeted by the present invention. A tissue or cell targeted by the present invention may be derived from any organ. As used herein, the term "organ" refers to a morphologically independent structure localized at a particular portion of an individual organism in which a certain function is performed. In multicellular organisms (e.g., animals, plants), an organ consists of several tissues spatially arranged in a particular manner, each tissue being composed of a number of cells. An example of such an organ includes an organ relating to the vascular system. In one embodiment, organs targeted by the present invention include, but are not limited to, skin, blood vessel, cornea, kidney, heart, liver, umbilical cord, intestine, nerve, lung, placenta, pancreas, brain, peripheral limbs, retina, and the like. Any organ may be herein used as a target. Preferably, mesenchymal tissue (e.g., fat, bone, ligament, etc.) may be targeted, without limitation.

As used herein, the term "conditions sufficient for differentiation" refers to time, medium, temperature, humidity, and the like which cause differentiation. The present invention is the first to find that by blending an adipose-derived precursor cell with a differentiated cell, the adipose-derived precursor cell is destined to become the differentiated cell. According to the present specification, it will be understood that such conditions overlap with conditions for maintaining adipose-derived precursor cells or differentiated cells singly. Therefore, the conditions may be changed as appropriate. Preferably, the conditions may be changed depending on the adipose-derived precursor cell of the present invention and a differentiated cell to be combined therewith and the composition of the mixture thereof. Once such preferable conditions are established, the conditions may be subsequently used for treatment of similar mixtures. In the present invention, such conditions for differentiation may be used for either in vitro, in vivo, or ex vivo situations. In the in viva case, conditions which are provided within the implanted site of the body are used as they are. In the present invention, immediately after a stem cell and a differentiated cell are mixed, the mixture may be implanted into an in vivo environment or may be co-cultured in vitro. Autologous transplantation may be called ex vivo transplantation.

As used herein, the term "in vivo" refers to within an organism(s). In a specific context, "in vivo" refers to a position at which a subject tissue or organ is placed (e.g., a desire site as used herein).

As used herein, "in vitro" indicates that a part of an organism is extracted or released outside the organism for various purposes of research (e.g., in a test tube). The term in vitro is in contrast to the term in vivo.

As used herein, the term "ex vivo" refers to a series of operations where target cells into which a gene will be introduced are extracted from a subject; a therapeutic gene is introduced in vitro into the cells; and the cells are returned into the same subject.

An example of conditions for differentiation can be independently selected from the following: culture for 5 hours or more, pH of 5 to 10, temperature of 20° C. to 45° C. (e.g., 37° C.), humidity of 80% or more (e.g., 100%), use of M199 medium, supplement of 5 mg/500 ml heparin, supplement of 2 µg/500 ml acidic FGF, supplement of FBS (15%), supplement of $NaHCO_3$, oxygen concentration of 10 to 30% (e.g., 20%), $CO_2$ concentration of 2 to 10% (e.g., 5%), use of a gelatin coated dish, the presence of feeder cells, and the like. As an example, conditions are: culture for 5 hours, M199 medium (500 ml supplemented with 2.2 g of NaHCO$_3$, FBS (15%), 2 μg of acidic FGF, and 5 mg of heparin), at 37° C., 20% oxygen, 5% carbonic acid gas, 100% humidity, and culture in a gelatin coated dish. The present invention is not limited to this.

The above-described conditions may be used for the maintenance of differentiated cells (e.g., adipocytes) and adipose-derived precursor cells. The present invention is not limited to this.

For the differentiation of adipose-derived precursor cells, any culture medium containing an agent for promoting differentiation of the cells may be used for culture. Such a medium may be, for example, without limitation, DMEM supplemented with 10% FBS, 0.5 mM isobutylmethyl xanthine (IBMX), 1 μM dexamethasone, 10 μM insulin, and 200 μM indomethacin. The medium may be used at 37° C., 20% oxygen, 5% carbonic acid gas, and 100% humidity.

As used herein, the term "agent promoting the differentiation into a differentiated cell" or "differentiation promoting agent" refers to any agent which is known to promote differentiation into a differentiated cell (e.g., a chemical substance, temperature, etc.). Examples of such an agent include, but are not limited to, various environmental agents, such as temperature, humidity, pH, salt concentration, nutrients, metals, gas, organic solvents, pressure, chemical substances (e.g., steroids, antibiotics, etc.), and the like, or any combination thereof. Representative examples of such an agent include, but are not limited to, DNA demethylating agents (e.g., 5-azacytidine, etc.), histone deacetylating agents (e.g., trichostatin, etc.), intranuclear receptor ligands (e.g., retinoic acids (ATRA), vitamin D3, T3, etc.), cell growth factors (activin, IGF-1, FGF, PDGF, TGF-β, BMP2/4, etc.), cytokines (e.g., LIF, IL-2, IL-6, etc.), hexamethylenebisacetamide, dimethylacetamide, dibutyl cAMP, dimethylsulfoxide, iododeoxyuridine, hydroxyl urea, cytosine arabinoside, mitomycin C, sodium butyrate, aphidicholine, fluorodeoxyuridine, polybrene, selenium, etc. However, differentiated cells were not conventionally considered to be used as differentiation promoting agents. This is because differentiated cells release agents which suppress differentiation.

As used herein, the term "corresponding to a desired site" in relation to a cell, a tissue, an organ, or the like, which is intended to be used for implantation or regeneration according to the present invention, indicates that the cell or the like was obtained from the desired site (e.g., a heart-derived cell, etc.) or the cell or the like has substantially the same properties as those of a cell present at the desired site (e.g., a cell differentiated into a heart cell, etc.). Therefore, a cell can be confirmed to correspond to a desired site if the cell has substantially the same feature (e.g., a cell surface marker, etc.) as that of a cell at a desired site.

Examples of markers useful for the determination of a cell corresponding to such a desired site include, but are not limited to, (1) fat: the presence of triglycerides within cytoplasm, OilRed-O staining, glycerophosphatedehydrogenase (Glycerophosphate dehydrogenase=GPDH) activity, GLUT4 within cytoplasm, Ap2 (fatty acid binding protein), LPL (lipoprotein lipase), PPARγ1,2 (peroxisome growth activating receptor γ1,2), and the expression of leptin; (2) bone cell, bone tissue: the presence of alkaliphosphatase, the confirmation of the degree of bone calcification (precipitation of calcium), and the expression of osteocalcin, osteopontin, or osteonectin; (3) chondrocyte, cartilage tissue: the presence of mucopolysaccharides, the expression/presence of type II collagen, chondroitin-4-sulfate; (4) skeletal muscle cells: the presence of abundant myosin within cytoplasm; and the like.

As used herein, the term "implantation" refers to an insertion of the cell, composition, medicament, or the like of the present invention into the body singly or in combination with other therapeutic agents. In the present invention, the following method, form, and amount may be used for introduction into a therapy site (e.g., bone, etc.): the medicament of the present invention is directly injected into, adhered and stitched to, inserted into, or the like, an injured site. A combination of an adipose-derived precursor cell and a differentiated cell of the present invention may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously (e.g., a differentiation promoting agent, etc.). Administration "in combination" further includes the separate administration of one of the compounds or agents given first, followed by the second.

As used herein, the term "autologous" or "self" in relation to an entity refers to the whole or a part (e.g., a cell, a tissue, an organ, etc.) of the same entity. As used herein, the term "autologous" or "self" may encompass a graft from a genetically identical individual (e.g. an identical twin) in a broad sense.

As used herein, the term "allogenic" refers to the whole or a part (e.g., a cell, a tissue, an organ, etc.) of an entity which is implanted from another entity which is the same species but is genetically different. Since an allogenic entity is genetically different, the allogenic entity may elicit an immune reaction in an entity (recipient) to which the allo-entity is implanted. Such a cell includes, for example, without limitation, a cell derived from its parent.

As used herein, the term "heterologous" refers to a matter which is implanted from a different species entity. Therefore, for example, when a human is a recipient, a porcine-derived graft is called a heterologous graft.

As used herein, "recipient" (acceptor) refers to an entity which receives an implanted cell or the like and is also called "host". In contrast, an entity providing an implanted cell or the like is called "donor" (provider). A donor may be the same as or different from a recipient.

A cell used in the present invention may be derived from an autologous origin (syngeneic origin), an allogenic origin (non-self origin), or a heterologous origin. In view of rejection reactions, syngeneic cells are preferable. If rejection reactions do not raise problems, allogenic cells may be employed.

As used herein, the term "disease, disorder, or abnormal condition attributed to the deficiency of a differentiated cell" refers to any disease, disorder, or abnormal condition in which the differentiated cell is involved. Such a differentiated cell may be preferably, without limitation, a mesenchymal cell.

In one embodiment, diseases and disorders targeted by the present invention may be of the circulatory system (blood cells, etc.). Examples of the diseases or disorders include, but are not limited to, anemia (e.g., aplastic anemia (particularly, severe aplastic anemia), renal anemia, cancerous anemia, secondary anemia, refractory anemia, etc.), cancer or tumors (e.g., leukemia); and after chemotherapy therefor, hematopoietic failure, thrombocytopenia, acute myelocytic leukemia (particularly, a first remission (high-risk group), a second remission and thereafter), acute lymphocytic leukemia (particularly, a first remission, a second remission and thereafter), chronic myelocytic leukemia (particularly, chronic period, transmigration period), malignant lymphoma (particularly, a first remission (high-risk group), a second remission and thereafter), multiple myeloma (particularly, an early period after onset), and the like; heart failure, angina pectoris, myocardial infarct, arrhythmia, valvulitis, cardiac muscle/pericardium diseases, congenital heart diseases (e.g., atrial septal defect, arterial canal patency, tetralogy of Fallot, etc.), arterial diseases (e.g., arteriosclerosis, aneurysm), vein diseases (e.g., phlebeurysm, etc.), lymphoduct diseases (e.g., lymphedema, etc.), and the like.

In another embodiment, diseases and disorders targeted by the present invention may be of the nervous system. Examples of such diseases or disorders include, but are not limited to, dementia, cerebral stroke and sequela thereof, cerebral tumor, spinal injury, and the like.

In another embodiment, diseases and disorders targeted by the present invention may be of the immune system. Examples of such diseases or disorders include, but are not limited to, T-cell deficiency syndrome, leukemia, and the like.

In another embodiment, diseases and disorders targeted by the present invention may be of the motor organ and the skeletal system. Examples of such diseases or disorders include, but are not limited to, fracture, osteoporosis, luxation of joints, subluxation, sprain, ligament injury, osteoarthritis, osteosarcoma, Ewing's sarcoma, myodystrophy, osteogenesis imperfecta, osteochondrodysplasia, and the like.

In another embodiment, diseases and disorders targeted by the present invention may be of the skin system. Examples of such diseases or disorders include, but are not limited to, atrichia, melanoma, cutis malignant lympoma, hemangiosarcoma, histiocytosis, hydroa, pustulosis, dermatitis, eczema, and the like.

In another embodiment, diseases and disorders targeted by the present invention may be of the endocrine system. Examples of such diseases or disorders include, but are not limited to, hypothalamus/hypophysis diseases, thyroid gland diseases, accessory thyroid gland (parathyroid) diseases, adrenal cortex/medulla diseases, saccharometabolism abnormality, lipid metabolism abnormality, protein metabolism abnormality, nucleic acid metabolism abnormality, inborn error of metabolism (phenylketonuria, galactosemia, homocystinuria, maple syrup urine disease), analbuminemia, lack of ascorbic acid synthetic ability, hyperbilirubinemia, hyperbilirubinuria, kallikrein deficiency, mast cell deficiency, diabetes insipidus, vasopressin secretion abnormality, dwarfism, Wolman's disease (acid lipase deficiency)), mucopolysaccharidosis VI, and the like.

In another embodiment, diseases and disorders targeted by the present invention may be of the respiratory system. Examples of such diseases or disorders include, but are not limited to, pulmonary diseases (e.g., pneumonia, lung cancer, etc.), bronchial diseases, and the like.

In another embodiment, diseases and disorders targeted by the present invention may be of the digestive system. Examples of such diseases or disorders include, but are not limited to, esophagial diseases (e.g., esophagial cancer, etc.), stomach/duodenum diseases (e.g., stomach cancer, duodenum cancer, etc.), small intestine diseases/large intestine diseases (e.g., polyps of the colon, colon cancer, rectal cancer, etc.), bile duct diseases, liver diseases (e.g., liver cirrhosis, hepatit is (A, B, C, D, E, etc.), fulminant hepatit is, chronic hepatit is, primary liver cancer, alcoholic liver disorders, drug induced liver disorders, etc.), pancreatic diseases (acute pancreatitis, chronic pancreatitis, pancreas cancer, cystic pancreas diseases, etc.), peritoneum/abdominal wall/diaphragm diseases (hernia, etc.), Hirschsprung's disease, and the like.

In another embodiment, diseases and disorders targeted by the present invention may be of the urinary system. Examples of such diseases or disorders include, but are not limited to, kidney diseases (e.g., renal failure, primary glomerulus diseases, renovascular disorders, tubular function abnormality, interstitial kidney diseases, kidney disorders due to systemic diseases, kidney cancer, etc.), bladder diseases (e.g., cystitis, bladder cancer, etc.), and the like.

In another embodiment, diseases and disorders targeted by the present invention may be of the genital system. Examples of such diseases or disorders include, but are not limited to, male genital organ diseases (e.g., male sterility, prostatomegaly, prostate cancer, testicular cancer, etc.), female genital organ diseases (e.g., female sterility, ovary function disorders, hysteromyoma, adenomyosis uteri, uterine cancer, endometriosis, ovarian cancer, villosity diseases, etc.), and the like.

As used herein, the term "effective amount for diagnosis, prevention, treatment, or prognosis" refers to an amount which is recognized as being therapeutically effective for diagnosis, prevention, treatment (or therapy), or prognosis. Such an amount can be determined by those skilled in the art using techniques well known and considering various parameters.

In another embodiment, the present invention may be used in therapy, treatment, or improvement for cosmetic purposes. Such cosmetic purposes include, cosmetic therapy for postoperative or posttraumatic deformation and congential deformation as well as pure cosmetic purposes to healthy conditions. The present invention may be applied to, for example, without limitation, a technique for increasing breast tissue (breast augmentation), a technique for increasing cheek or upper and lower eyelids to compensate for hollow, and a technique for increasing tissue to compensate for tissue atrophy after facial hemiatrophy or facial paralysis, or funnel breast. Further, the present invention may be applied to, for example, without limitation, rhinoplasty, reduction rhinoplasty, genioplasty (tissue augmentation), metopeplasty (tissue augmentation), auriclular chondroplasty for deformation/malformation of auricle, such as microtia, and the like.

Any animal which has adipocytes may be targeted by the present invention (e.g., Myxiniformes, Petronyzoniformes, Chondrichthyes, Osteichthyes, Amphibia, Reptilia, Aves, Mammalia, etc.). Preferably, such an animal may be a mammalian animal (e.g., Monotremata, Marsupialia, Edentate, Dermoptera, Chiroptera, Carnivora, Insectivora, Proboscidea, Perissodactyla, Artiodactyla, Tubulidentata, Pholidota, Sirenia, Cetacean, Primates, Rodentia, Lagomorpha, etc.). Illustrative subjects include, but are not limited to, animals such as bovines, pigs, horses, chickens, cats, dogs and the like. More preferably, primates (e.g., chimpanzee, Japanese monkey, human, etc.) may be used. Most preferably, a human may be used.

When the present invention is used as a medicament, the medicament may further comprise a pharmaceutically acceptable carrier. Any pharmaceutically acceptable carrier known in the art may be used in the medicament of the present invention.

Examples of a pharmaceutical acceptable carrier or a suitable formulation material include, but are not limited to, antioxidants, preservatives, colorants, flavoring agents, diluents, emulsifiers, suspending agents, solvents, fillers, bulky agents, buffers, delivery vehicles, and/or pharmaceutical adjuvants. Representatively, a medicament of the present invention is administered in the form of a composition comprising a cell of the present invention and other active ingredients, with at least one physiologically acceptable carrier, exipient or diluent. For example, an appropriate vehicle may be injection solution, physiological solution, or artificial cerebrospinal fluid, which can be supplemented with other substances which are commonly used for compositions for parenteral delivery.

Acceptable carriers, excipients or stabilizers used herein preferably are nontoxic to recipients and are preferably inert at the dosages and concentrations employed, and preferably include phosphate, citrate, or other organic acids; ascorbic acid, α-tocopherol; low molecular weight polypeptides; proteins (e.g., serum albumin, gelatin, or immunoglobulins); hydrophilic polymers (e.g., polyvinylpyrrolidone); amino acids (e.g., glycine, glutamine, asparagine, arginine or lysine); monosaccharides, disaccharides, and other carbohydrates (glucose, mannose, or dextrins); chelating agents (e.g., EDTA); sugar alcohols (e.g., mannitol or sorbitol); salt-forming counterions (e.g., sodium); and/or nonionic surfactants (e.g., Tween, pluronics or polyethylene glycol (PEG)).

Examples of appropriate carriers include neutral buffered saline or saline mixed with serum albumin. Preferably, the product is formulated as a lyophilizate using appropriate excipients (e.g., sucrose). Other standard carriers, diluents, and excipients may be included as desired. Other exemplary compositions comprise Tris buffer of about pH 7.0-8.5, or acetate buffer of about pH 4.0-5.5, which may further include sorbitol or a suitable substitute therefor.

General techniques for preparing the medicament composition of the present invention will be described below. Note that animal drug compositions, quasi-drug compositions, marine drug compositions, food compositions, cosmetic compositions, and the like can be produced by known techniques.

The cell and the like of the present invention can be optionally mixed with a pharmaceutically acceptable carrier and can be parenterally administered as liquid formulations (e.g., injections, suspensions, solutions, spray agents, etc.). Examples of pharmaceutically acceptable carriers include excipients, lubricants, binders, disintegrants, disintegration inhibitors, absorption promoters, adsorbers, moisturizing agents, solvents, solubilizing agents, suspending agents, isotonic agents, buffers, soothing agents and the like. Additives for formulations, such as antiseptics, antioxidants, colorants, sweeteners, and the like can be optionally used. The composition of the present invention can be mixed with substances other than the polynucleotides, polypeptides, and the like of the present invention. Examples of parenteral routes of administration include, but are not limited to, intravenous, intramuscular, subcutaneous, intradermal, intramucosal, intrarectal, intravaginal, topically, percutaneous routes, and the like. When systemically administered, a medicament for use in the present invention may be in the form of a pyrogen-free, pharmaceutically acceptable aqueous solution. The preparation of such pharmaceutically acceptable compositions, with due regard to pH, isotonicity, stability and the like, is within the skill of the art.

Preferable examples of solvents in liquid formulations include injection solutions, alcohols, propyleneglycol, macrogol, sesame oil, corn oil, and the like.

Preferable examples of solubilizing agents in liquid formulations include, but are not limited to, polyethyleneglycol, propyleneglycol, D-mannitol, benzyl benzoate, ethanol, trisaminomethane, cholesterol, triethanolamine, sodium carbonate, sodium citrate, and the like.

Preferable examples of suspending agents in liquid formulations include surfactants (e.g., stearyltriethanolamine, sodium lauryl sulfate, lauryl amino propionic acid, lecithin, benzalkonium chloride, benzethonium chloride, glycerin monostearate, etc.), hydrophilic macromolecule (e.g., polyvinyl alcohol, polyvinylpyrrolidone, carboxymethylcellulose sodium, methylcellulose, hydroxymethylcellulose, hydroxyethylcellulose, hydroxyethylcellulose, hydroxypropylcellulose, etc.), and the like.

Preferable examples of isotonic agents in liquid formulations include, but are not limited to, sodium chloride, glycerin, D-mannitol, and the like.

Preferable examples of buffers in liquid formulations include, but are not limited to, phosphate, acetate, carbonate, citrate, and the like.

Preferable examples of soothing agents in liquid formulations include, but are not limited to, benzyl alcohol, benzalkonium chloride, procaine hydrochloride, and the like.

Preferable examples of antiseptics in liquid formulations include, but are not limited to, para hydroxybenzoate esters, chlorobutanol, benzyl alcohol, 2-phenylethylalcohol, dehydroacetic acid, sorbic acid, and the like.

Preferable examples of antioxidants in liquid formulations include, but are not limited to, sulfite, ascorbic acid, α-tocopherol, cysteine, and the like.

When liquid agents and suspensions are prepared as injections, they are sterilized and are preferably isotonic with the blood or a medium at an injection site for other purposes. Typically, these agents are made aseptic by filtration using a bacteria-retaining filter or the like, mixing with a bactericide or, irradiation, or the like. Following this treatment, these agents may be made solid by lyophilization or the like. Immediately before use, sterile water or sterile injection diluent (aqueous lidocaine hydrochloride solution, physiological saline, aqueous glucose solution, ethanol or a mixture thereof, etc.) may be added.

The medicament composition of the present invention may further comprise a colorant, a preservative, an aromatic chemical, a flavor, a sweetener, or other drugs.

The amount of a composition used in the treatment method of the present invention can be easily determined by those skilled in the art with reference to the purpose of use, target disease (type, severity, and the like), the patient's age, weight, sex, and case history, the form or type of the cell, and the like. The frequency of the treatment method of the present invention applied to a subject (or patient) is also determined by those skilled in the art with respect to the purpose of use, target disease (type, severity, and the like), the patients age, weight, sex, and case history, the progression of the therapy, and the like. Examples of the frequency include once per day to several months (e.g., once per week to once per month). Preferably, administration is performed once per week to month with reference to the progression. A dose can be determined by estimating an amount which is required by a site to be treated.

As used herein, the term "instructions" describe a method of administering a medicament, a method for diagnosis, or the like of the present invention for persons who administer, or are administered, the medicament or the like or persons who diagnose or are diagnosed (e.g., physicians, patients, and the like). The instructions describe a statement indicating an appropriate method for administering a diagnostic, a medicament, or the like of the present invention. The instructions are prepared in accordance with a format defined by an authority of a country in which the present invention is practiced (e.g., Health, Labor and Welfare Ministry in Japan, Food and Drug Administration (FDA) in the U.S., and the like), explicitly describing that the instructions are approved by the authority. The instructions are so-called package insert and are typically provided in paper media. The instructions are not so limited and may be provided in the form of electronic media (e.g., web sites, electronic mails, and the like provided on the Internet).

The judgment of termination of treatment with a method of the present invention may be supported by a result of a standard clinical laboratory test using commercially available assays or instruments or extinction of a clinical symptom characteristic to a disease relevant to the intended treatment (e.g., bone diseases heart diseases, neurological diseases, etc.) or recovery of cosmetic states (e.g., recovery of appearance, etc.). Therapy may be resumed due to the relapse of diseases associated with the deficiency of differentiated cells or the like (e.g., neurological diseases) or the damage of cosmetic conditions.

The present invention also provides a pharmaceutical package or kit comprising one or more containers filled with one or more pharmaceutical compositions. A notice in a form defined by a government agency which regulates the production, use or sale of pharmaceutical products or biological products may be arbitrarily attached to such a container, representing the approval of the government agency relating to production, use or sale with respect to administration to humans. The kit may comprise an injecting device.

Toxicity studies may be carried out by measuring a blood cell composition. For example, a toxicity study may be carried out in the following appropriate animal model: (1) a compound is administered into mice (an untreated control mouse should also be used); (2) a blood sample is periodically obtained from a mouse in each treatment group via the tail vein; and (3) the sample is analyzed for the numbers of erythrocytes and leukocytes, the blood cell composition, and the abundance ratio of lymphocytes and polymorphonuclear cells. Comparison of the result of each drug regimen with the control shows whether or not toxicity is present.

At the end of each toxicity study, a further study may be carried out by sacrificing the animal (preferably, in accordance with American Veterinary Medical Association guidelines Report of the American Veterinary Medical Assoc. Panel on Euthanasia, (1993) J. Am. Vet. Med. Assoc. 202: 229-249). Thereafter, a representative animal from each treatment group may be tested by viewing the whole body for direct evidence of transitions, abnormal diseases or toxicity. A global abnormality in tissue is described and the tissue is histologically tested. A compound causing a reduction in weight or a reduction in blood components is not preferable as are compounds having an adverse action in major organs. In general, the greater the adverse action, the less preferable the compound.

(Description of Preferred Embodiments)

Hereinafter, preferred embodiments of the present invention will be described. The following embodiments are provided for a better understanding of the present invention and the scope of the present invention should not be limited to the following description. It will be clearly appreciated by those skilled in the art that variations and modifications can be made without departing from the scope of the present invention with reference to the specification.

(Methods for Preparing Differentiated Cells)

In one aspect, the present invention provides a method for preparing a differentiated cell. With this method, a differentiated cell having a desired property, preferably uniformly, can be provided in a predetermined amount or more. The method comprises the steps of: A) mixing a) an adipose-derived precursor cell and b) a differentiated cell corresponding to a desired site to obtain a mixture; and B) culturing the mixture under conditions sufficient for differentiation of the adipose-derived precursor cell.

Adipose-derived precursor cells can be isolated from the fat portion of aspirates (lipoaspirates) from liposuction as follows (e.g., WO00/53795; WO03/022988; WO01/62901; Zuk, P. A., et al., Tissue Engineering, Vol. 7, 211-228, 2001; Zuk, P. A., et al., Molecular Biology of the Cell Vol. 13, 4279-4295, 2002; or modifications thereof. Specifically, for example, (1) suctioned fat is washed well with physiological saline using a 1-liter separatory funnel; (2) the sufficient separation of the suctioned fat in the upper layer from the physiological saline in the lower layer is confirmed, and thereafter, the lower layer is discarded. This procedure is repeated until the physiological saline becomes substantially transparent when viewed with the naked eye; (3) 0.075% collagenase/PBS is added in an amount equal to that of the suctioned fat, followed by incubation at 37° C. for 30 minutes while stirring well; (4) an equal amount of 10% serum-supplemented DMEM is added to the above-described sample; (5) the sample is centrifuged at 1200×g for 10 minutes; (6) the resultant pellet is suspended in 0.16 M $NH_4Cl$/PBS, followed by incubation at room temperature for 10 minutes; (7) the sample is subjected to suction filtration using a 100 μm-diameter mesh; and (8) the resultant filtrate is centrifuged at 1200×g for 5 minutes. The above-described protocol may be scaled up or down by those skilled in the art, depending on the amount of formulation.

On the other hand, adipose-derived precursor cells can be isolated from the liquid portion of aspirates (liquid aspirates) from liposuction, for example, as follows: (1) a liquid portion of aspirates from liposuction is prepared; (2) the liquid portion is centrifuged to obtain a cell fraction; (3) the cell fraction is subjected to density gradient centrifugation, and cell separation is performed based on the specific gravity; and (4) cells are collected from a cell layer having a specific gravity lower than that of an erythrocyte. The liquid portion of aspirates may be prepared using physiological saline or Ringer's injection. The centrifugation may be performed at a rate of about 800×g or less, or alternatively, about 400×g or more. The density gradient centrifugation is performed at a rate of about 370×g to 1,100×g. The density gradient centrifugation is performed using a medium having a specific gravity (20° C.) of about 1.076 to 1.078 g/ml. The medium used in the density gradient centrifugation may be Ficoll™, Percoll™, or sucrose. The specific gravity of the collected cell layer may be in the range of about 1.050 to 1.075. The cell layer may be collected using a pipette.

A differentiated cell corresponding to a desired site can be prepared using techniques well known in the art. Alternatively, such a differentiated cell may be available from commercially available cell lines (e.g., cell lines obtained from the ATCC or the like, etc.). Such a differentiated cell may be obtained from primary cultured cells from a subject in need of implantation (e.g., hepatic cells, renal cells, adipocytes, bone cells, chondrocytes, etc.). Techniques for primary culture and cell line culture are well known in the art as described in, for example, Hiroshi Hatanaka & Akira Asano, eds., "AMBO Manuaru Saibo Kenkyuho [AMBO Manual of Cell Study Methods]", TaKaRa; Toshio Watanabe, ed., "Baio Jikken Irasutoreiteddo (6) Sukusuku Sodate Saibo Baiyo [Illustrated Culture Experiments—Cells grow quickly]", Shujun sha (1996); and the like, which are herein incorporated by reference.

In the present invention, any differentiated cell corresponding to a desired site may be used. Preferably, mesenchymal cells may be used. Examples of mesenchymal cells include, but are not limited to, adipocytes, bone marrow cells, osteoblasts, chondrocytes, fibroblasts, myofibroblasts, nerve cells, skeletal muscle cells, cardiac muscle cells, vascular endothelial cells, vascular smooth muscle cells, hepatic cells, renal cells, and the like. The differentiated cell may be an identified cell. Alternatively, the differentiated cell may be a cell having unidentified properties, which can be prepared by using an isolation technique, such as FACS, with a marker. Examples of such a marker: (1) fat: the presence of triglyceride within cytoplasm, OilRed-O staining, glycerophosphatedehydrogenase (GPDH) activity, GLUT4 within cytoplasm, Ap2 (fatty acid binding protein), LPL (lipoprotein lipase), PPARγ1, 2 (peroxisome growth activating receptor γ1,2), and the expression of leptin; (2) bone cell, bone tissue: the presence of alkaliphosphatase, the confirmation of the degree of bone calcification (precipitation of calcium), and the expression of osteocalcin, osteopontin, or osteonectin; (3) chondrocyte, cartilage tissue: the presence of mucopolysaccharide, the expression/presence of type II collagen, chondroitin-4-sulfate; (4) skeletal muscle cells: the presence of abundant myosin within cytoplasm; and the like. FACS protocols are described in, for example, Nakauchi, ed., "Furosaitometori Jiyujizai [Master of Flow cytometery]", Special Issue, Saibokogaku [Cell Engineering] (Shujunsha), 1999; and the like, which is herein incorporated by reference.

A cell mixture of the present invention may further comprise an agent for promoting differentiation into a differentiated cell corresponding to a desired site. Such an agent may be any one which is known or confirmed to promote differentiation into a differentiated cell corresponding to a desired site. Examples of preferable differentiation promoting agents include, but are not limited to, adrenocortical steroids (e.g., dexamethasone, etc.), insulin, glucose, indomethacin, isobutyl-methylxanthine (IBMX), ascorbate-2-phosphate (ascorbate-2-phosphate), ascorbic acid and a derivative thereof, glycerophosphate, estrogen and a derivative thereof, progesterone and a derivative thereof, androgen and a derivative thereof, growth factors (e.g., aFGF, bFGF, EGF, IGF, TGF-β, ECGF, BMP, PDGF, etc.), a pituitary gland extract, a pineal body extract, retinoic acid, vitamin D, thyroid hormone, fetal bovine serum, equine serum, human serum, heparin, sodium hydrogen carbonate, HEPES, albumin, transferrin, selenic acid (e.g., sodium selenite, etc.), linoleic acid, 3-isobutyl-1-methylxanthine, demethylating agents (e.g., 5-azacytidine, etc.), histone deacetylating agents (e.g., trichostatin, etc.), activin, cytokines (e.g., LIF, IL-2, IL-6, etc.), hexamethylene bisacetamide (HMBA), dimethylacetamide (DMA), dibutyl cAMP (dbcAMP), dimethyl sulfoxide (DMSO), iododeoxyuridine (IdU), hydroxyurea (HU), cytosine arabinoside (AraC), mitomycin C (MMC), sodium butyrate (NaBu), polybrene, selenium, and the like.

For the cell mixture of the present invention, any culture medium may be used as long as mixed cells can be maintained and differentiation into a differentiated cell corresponding to a desired site can be maintained. Examples of such a culture medium include, but are not limited to, DMEM, P199, MEM, HBSS (Hanks' Balanced Salt Solution), Ham's F12, BME, RPMI1640, MCDB104, MCDB153 (KGM), and the like. Such a culture medium may be supplemented with adrenocortical steroids (e.g., dexamethasone (dexamethasone), etc.), insulin, glucose, indomethacin, isobutyl-methylxanthine (IBMX), ascorbate-2-phosphate (ascorbate-2-phosphate), ascorbic acid and a derivative thereof, glycerophosphate (glycerophosphate), estrogen and a derivative thereof, progesterone and a derivative thereof, androgen and a derivative thereof, growth factors (e.g., aFGF, bFGF, EGF, IGF, TGF-β, ECGF, BMP, PDGF, etc.), an extract of pituitary gland, an extract of pineal body, retinoic acid, vitamin D, thyroid hormone, fetal bovine serum, equine serum, human serum, heparin, sodium hydrogen carbonate, HEPES, albumin, transferrin, selenic acid (e.g., sodium selenite, etc.), linoleic acid, 3-isobutyl-1-methylxanthine, demethylating agents (e.g., 5-azacytidine, etc.), histone deacetylating agents (e.g., trichostatin, etc.), activin, cytokines (e.g., LIF, IL-2, IL-6, etc.), hexamethylene bisacetamide (HMBA), dimethylacetamide (DMA), dibutyl cAMP (dbcAMP), dimethyl sulfoxide (DMSO), iododeoxyuridine (IdU), hydroxyurea (HU), cytosine arabinoside (AraC), mitomycin C (MMC), sodium butyrate (NaBu), polybrene, selenium, and the like, alone or in combination.

An adipose-derived precursor cell used in the present invention may be one that can express at least one selected from the group consisting of proteins CD13, CD29, CD34, CD36, CD44, CD49d, CD54, CD58, CD71, CD73, CD90, CD105, CD106, CD151, and SH3 (preferably, two, three, . . . , n proteins). More preferably, an adipose-derived precursor cell used in the present invention is one that can express all of CD13, CD29, CD34, CD36, CD44, CD49d, CD54, CD58, CD71, CD73, CD90, CD105, CD106, CD151, and SH3. It was revealed that these stem cells are novel and are useful in regenerative therapy (particularly, breast augmentation, pastoplasty) in the present invention.

These CD antigens can be detected with techniques known in the art (e.g., immunological techniques using antibodies, etc.). Their expression can be determined using immunological techniques or the like.

Preferably, an adipose-derived precursor cell used in the present invention may not express at least one of CD3, CD4, CD14, CD15, CD16, CD19, CD33, CD38, CD56, CD61, CD62e, CD62p, CD69, CD104, CD135, and CD144 (particularly, CD56). These CD antigens serve as markers for differentiated cells. The absence of expression in a cell indicates that the cell is a stem cell. The present invention is not limited to this. Therefore, in a preferred embodiment, an adipose-derived precursor cell used in the present invention may be advantageously a cell which expresses none of CD3, CD4, CD14, CD15, CD16, CD19, CD33, CD38, CD56, CD61, CD62e, CD62p, CD69, CD104, CD135, and CD144.

In another embodiment, simply, an adipose-derived precursor cell which expresses CD49d but not CD56 may be selected.

In a preferred embodiment of the method of the present invention, the abundance ratio of an adipose-derived precursor cell to a differentiated cell corresponding to a desired site, which are used in the present invention, may be advantageously higher than the abundance ratio of a stem cell to the differentiated cell in healthy tissue. In this case, for example, it was demonstrated that when suctioned fat is used, the higher proportion of an adipose-derived precursor cell in the suctioned fat than the in vivo proportion can lead to an increase in cosmetic effect. Such a proportion of an adipose-derived precursor cell present can be represented by a relative ratio to the proportion of naturally-occurring adipose-derived precursor cells. Therefore, preferably, an adipose-derived precursor cell used in the cell mixture or composition of the present invention, has a higher proportion than that in naturally-occurring tissue. Such a ratio may be, for example, without limitation, typically at least about 1.1 times, at least about 1.2 times, at least about 1.3 times, at least about 1.4 times, at least about 1.5 times, at least about 2 times, at least about 3 times, at least about 4 times, at least about 5 times, or preferably at least about 10 times the proportion in naturally-occurring fat tissue. Preferably, the ratio may be in the range of about 2 to 10 times the proportion in naturally-occurring fat tissue. Though not wishing to be bound by any theory, this is because, typically, some of the stem cells, which are inherently or preliminarily present in tissue to be treated, have already been consumed or undergone necrosis (i.e., the number of stem cells is reduced). Stem cells are consumed so as to repair tissue damaged due to tissue necrosis, mechanical impairments, impaired circulation, chronic inflammation, or the like. In this case, the reserve cell generating capacity of tissue is reduced.

An adipose-derived precursor cell used in the present invention may be derived from suctioned fat. Conventionally, suctioned fat is discarded. In the present invention, it was revealed that suctioned fat can be used as a supply source of stem cells which can be actually used in therapy and cosmesis. Therefore, such suctioned fat may be, for example, a liquid portion or a fat portion of an aspirate from liposuction.

(Cell Mixture)

In another aspect, the present invention provides a cell mixture comprising an adipose-derived precursor cell and a differentiated cell corresponding to a desired site. Such a cell mixture is useful for cell implantation. Advantageously, the present invention requires a smaller number of components as compared with conventional techniques in which a differentiated cell is used singly. In addition, the present invention has the following advantageous features over conventional techniques: (1) production of regenerated tissue outside the body (ex vivo production) is not required; (2) a larger tissue can be regenerated more reliably; (3) regeneration can be achieved simply and quickly; (4) incision operation is not required for an organ, such as skin or the like, and cells and tissue can be administered (implanted) by needle puncture; and the like.

The cell mixture may be preferably exposed under conditions sufficient for differentiation of adipose-derived precursor cells before implantation. The present invention is not limited to this. Cells which have already been differentiated may be directly used for implantation. Alternatively, cells may be used after the cells have been differentiated into tissue or an organ.

In a preferred embodiment of the cell mixture of the present invention, the abundance ratio of an adipose-derived precursor cell to a differentiated cell corresponding to a desired site, which are used in the present invention, may be advantageously higher than the abundance ratio of a stem cell to the differentiated cell in healthy tissue. In this case, for example, it was demonstrated that when suctioned fat is used, the higher proportion of an adipose-derived precursor cell in the suctioned fat than the in vivo proportion can lead to an increase in a cosmetic effect. Such an abundance ratio of an adipose-derived precursor cell to a differentiated cell corresponding to a desired site may be, for example, without limitation, typically 0.1:1 to 5:1, and preferably 1:1 to 5:1. Such a proportion of an adipose-derived precursor cell present can be represented by a relative ratio to the proportion of naturally-occurring adipose-derived precursor cells. Therefore, preferably, an adipose-derived precursor cell used in the present invention, in the cell mixture or composition of the present invention, has a higher proportion than that in naturally-occurring tissue. Such a ratio may be, for example, without limitation, typically at least about 1.1 times, at least about 1.2 times, at least about 1.3 times, at least about 1.4 times, at least about 1.5 times, at least about 2 times, at least about 3 times, at least about 4 times, at least about 5 times, or preferably at least about 10 times the proportion in naturally-occurring fat tissue.

An adipose-derived precursor cell used in the present invention may be derived from suctioned fat. Conventionally, suctioned fat is discarded. In the present invention, it was revealed that suctioned fat can be used as a supply source of stem cells which can be actually used in therapy and cosmesis. Therefore, such suctioned fat may be, for example, a liquid portion or a fat portion of an aspirate from liposuction.

A differentiated cell and an adipose-derived precursor cell used in the present invention may be isolated, or alternatively, may be partially or fully purified.

In a preferred embodiment, a differentiated cell corresponding to a desired site, which is contained in the cell mixture of the present invention, may be an adipocyte. In this case, the adipocyte can be prepared from fat of a portion unwanted by people of today (e.g., fat of abdomen, chest, buttocks, thigh, upper arm, face, or the like). Abdomen, buttocks and the like are preferable. This is because abdomen, buttocks and the like tends to put on fat and such fat is often desired to be removed.

(Cell Implantation Composition)

In another aspect, the present invention provides a composition for cell implantation, comprising: a) an adipose-derived precursor cell; and b) a differentiated cell corresponding to a desired site. The composition may be used for any purpose in which it is desirable to treat or prevent diseases, disorders or abnormal conditions associated with the deficiency or deterioration of a differentiated cell corresponding to a desired site or to treat or improve cosmetic conditions. Preferably, the composition may be implanted into a desired site. The present invention is not limited to this. The composition may be administered or implanted into any site as long as it is possible to eventually treat or prevent a desired site.

The composition of the present invention has any abundance ratio of the adipose-derived precursor cell and the differentiated cell as long as the composition can elicit desired differentiation. The ratio ray be typically about 1:100 to about 100:1, representatively about 1:10 to about 10:1, preferably about 1:5 to about 5:1, more preferably about 1:2 to about 2:1, and most preferably about 1:1. The differentiated cell and the adipose-derived precursor cell used in the cell mixture may be herein in any form as described in the "Methods for preparing differentiated cells" and "Cell mixture" sections.

The differentiated cell and the adipose-derived precursor cell each are heterologous, allogenic, or isologous to a host to which they are implanted. Preferably, they are allogenic or isologous, and more preferably isologous. The present invention is not limited to this. Though not wishing to be bound by any theory, this is because it is possible to suppress immune rejection responses. However, if a rejection response is expected, the present invention may further comprise avoiding the rejection response. Procedures for avoiding rejection reactions are known in the art (see, for example, "Shin Gekagaku Taikei, Dai 12 Kan, Zoki Ishoku (Shinzo Ishoku Hai Ishoku Gijutsuteki, Rinriteki Seibi kara Jisshi ni Mukete [New Whole Surgery, Vol. 12, Organ Transplantation (Heart Transplantation Lung Transplantation From Technical and Ethical Improvements to Practice)" (Revised 3rd ed.), Nakayama Shoten]. Examples of such methods include, but are not limited to, a method using immunosuppressants or steroidal drugs, and the like. For example, there are currently the following immunosuppressants for preventing rejection reactions: "cyclosporine" (SANDIMMUNE/NEORAL); "tacrolimus" (PROGRAF); "azathioprine" (IMURAN); "steroid hormone" (prednine, methylprednine); and "T-cell antibodies" (OKT3, ATG, etc.). A method which is used worldwide as a preventive immunosuppression therapy in many facilities, is the concurrent use of three drugs: cyclosporine, azathioprine, and a steroid hormone. An immunosuppressant is desirably administered concurrently with a pharmaceutical agent of the present invention. The present invention is not limited to this. An immunosuppressant may be administered before or after a regeneration/therapeutic method of the present invention as long as an immunosuppression effect can be achieved.

The differentiated cell and the adipose-derived precursor cell each are heterologous, allogenic, or isologous, preferably allogenic or isologous, and more preferably isologous. Though not wishing to be bound by any theory, this is because a differentiated cell and an adipose-derived precursor cell, which are allogenic or isologous (preferably isologous), are likely to form a homogenous cell group.

The above-described cell mixture or composition may be provided as a medicament. Such a medicament may be used for treatment or prevention of diseases, disorders or abnormal conditions associated with the deficiency or deterioration of a differentiated cell corresponding to a desired site, or treatment or improvement of cosmetic conditions. The medicament of the present invention may comprise a pharmaceutically acceptable carrier in addition to the cell mixture or a composition comprising the same. As such a carrier, any carrier as described herein can be selected and used by those skilled in the art, depending on the purpose. In order to improve beauty, such a medicament may be preferably used in cosmetic treatment of a site in need of enhancement of fat. Such a site includes, but is not limited to, chest (including breast), buttocks, face (orthopedics, etc.), the dorsum of the hands, and the like, but varies depending on the subject who has an operation.

In a preferred embodiment, a differentiated cell corresponding to a desired site, which is contained in the composition of the present invention, may be an adipocyte. In this case, the adipocyte can be prepared from fat of a portion where that fat is unwanted by people of contemporary society (e.g., fat of abdomen, chest, buttocks, thigh, upper arm, face, or the like). Abdomen, buttocks and the like are preferable. This is because abdomen, buttocks and the like are areas that tend to put on fat and it is often desired to remove such fat.

(Therapy, Cosmesis, and Preventative Method Using Cell Mixture)

In another aspect, the present invention provides a method for treatment or prevention of diseases, disorders or abnormal conditions associated with the deficiency or deterioration of a differentiated cell corresponding to a desired site or treatment or improvement of cosmetic conditions, comprising the steps of: A) providing a composition comprising: a) an adipose-derived precursor cell; and b) a differentiated cell corresponding to a desired site; and B) administering the composition to a subject. The differentiated cell and the adipose-derived precursor cell used in the cell mixture for implantation may be herein in any form as described in the "Methods for preparing differentiated cells" and "Cell mixture" sections.

In a preferred embodiment, a differentiated cell corresponding to a desired site, which is contained in the cell mixture or composition of the present invention, may be an adipocyte. In this case, the adipocyte can be prepared from fat of a portion unwanted by people of today (e.g., fat of abdomen, chest, buttocks, thigh, upper arm, face, or the like). Abdomen, buttocks and the like are preferable. This is because abdomen, buttocks and the like tends to put on fat and such fat is often desired to be removed.

In the method of the present invention, in order to improve beauty, the composition may be preferably used in cosmetic treatment of a site in need of enhancement of fat. Such a site includes, but is not limited to, chest (including breast), buttocks, face (orthopedics, etc.), the dorsum of the hands, and the like, but varies depending on the subject who has the operation. In a preferred embodiment, the step of obtaining fat in the method of the present invention may be preferably performed by suctioning fat.

More preferably, the method of the present invention may comprise obtaining a differentiated cell corresponding to a desired site from fat of a subject to be treated. This is because immune rejection responses can be avoided. Further, in this case, fat which the subject wishes to remove can be removed, and the cell can be implanted into the site, for which enhancement is desired, with high efficiency and affinity. It is demonstrated that the method of the present invention provides an improved course after operation as compared to conventional techniques in which fat is suctioned and used without modification.

In a preferred embodiment, the method of the present invention may further comprise obtain an adipose-derived precursor cell, which is used in the method of the present invention, from the abdomen of the subject. In this case, the adipocyte can be prepared from fat of a portion unwanted by people of today (e.g., fat of abdomen, chest, buttocks, thigh, upper arm, face, or the like). Abdomen, buttocks and the like are preferable. This is because abdomen, buttocks and the like tends to put on fat and such fat is often desired to be removed. Such removal may be, for example, without limitation performed by suctioning. Suctioned fat containing adipose-derived precursor cells may be used without modification, or alternatively, adipose-derived precursor cells may be obtained from a liquid portion or a fat portion of an aspirate from liposuction.

The composition may be administered by any method known in the art. For example, without limitation, the composition may be injected using a syringe, a catheter, a tube, or the like. Preferably, exemplary routes of administration include, but are not limited to, local injection (subcutaneous injection, intraorgan injection (e.g., muscle, fat, etc.), intravenous injection, intraarterial injection, administration onto tissue, and the like. The treatment or preventative method of the present invention by implantation has the following advantages over conventional techniques, for example, without limitation: (1) production of regenerated tissue outside the body (ex vivo production) is not required; (2) a larger tissue can be regenerated more reliably; (3) regeneration can be achieved simply and quickly; (4) incision operation is not required for an organ, such as skin or the like, and cells and tissue can be administered (implanted) by needle puncture; and the like.

(Use)

In another aspect, the present invention provides use of a mixture of a) an adipose-derived precursor cell and b) a differentiated cell corresponding to a desired site for treatment or prevention of diseases, disorders or abnormal conditions associated with the deficiency or deterioration of a differentiated cell corresponding to a desired site or treatment or improvement of cosmetic conditions for cell implantation. The differentiated cell and the adipose-derived precursor cell used in the cell mixture for implantation may be herein in any form as described in the "Methods for preparing differentiated cells", "Cell mixture", and "Therapy, cosmesis, and preventative method using cell mixture" sections.

Hereinafter, the present invention will be described by way of examples. Examples described below are provided only for illustrative purposes. Accordingly, the scope of the present invention is not limited by the above-described embodiments or the examples below except as by the appended claims.

EXAMPLES

Reagents used in the examples below were obtained from Wako Pure Chemical Industries or Sigma unless otherwise specified. Animals were cared for in compliance with the spirit of animal protection in accordance with "Principles of Laboratory Animal Care" prepared by National Society for Medical Research and "Guide for the Care and Use of Laboratory Animals" (NIH Publication No. 86-23, 1985 revised) prepared by Institute of Laboratory Animal Resource and published by National Institute of Health. Informed consent was obtained from human subjects before any experiment.

Example 1

Preparation of Adipose-derived Precursor Cell Using Collagenase

In this example, adipose-derived precursor cells were prepared from fat which was suctioned from a human who gave informed consent for the experiment. Specifically, suctioned fat was washed well with physiological saline using a 1-liter separatory funnel; the sufficient separation of the suctioned fat in the upper layer from the physiological saline in the lower layer was confirmed, and thereafter, the lower layer was discarded; and this procedure was repeatedly performed until the physiological saline became substantially transparent when viewed with the naked eye, in this example 5 times.

0.075% collagenase/PBS was added in an amount equal to that of the suctioned fat, followed by incubation at 37° C. for 30 minutes while stirring well. An equal amount of 10% serum-supplemented DMEM was added to the sample, and the sample was centrifuged at 1200×g for 10 minutes.

The resultant pellet was suspended in 0.16 M $NH_4Cl$/PBS, followed by incubation at room temperature for 10 minutes. The sample was subjected to suction filtration using a 100 μm-diameter mesh (Whatman). The resultant filtrate was centrifuged at 1200×g for 5 minutes. The resultant cell formulate is also referred to as PLA. A cell marker (e.g., CD4, CD13, CD34, CD36, CD49d, CD71, CD90, CD105, CD117, CD151, etc.) was used to determine whether or not a cell was a stem cell.

Example 2

Preparation of Cell Suspension from a Liquid Portion of an Aspirate from Liposuction Stem cell suspension was prepared by processing a liquid portion of an aspirate from liposuction using either of the following two methods. In any of the two methods, treatment using an enzyme, such as collagenase or the like, is not required. Therefore, these methods are different from conventional methods in there is no contamination of an enzyme, such as collagenase or the like.

(I) Preparation Method 1

1) A liquid portion of an aspirate f rom liposuction (typically, about 2 to 4 liters) was centrifuged at 400×g for 10 minutes.

2) The supernatant was discarded. Note that as the precipitated cells were likely to float, an aspirator was used to carefully perform suction without damaging cells.

3) The precipitated cells (mostly, erythrocytes) were transferred to several 50-ml polypropylene tubes, followed by centrifugation (400×g, 5 min).

4) The supernatant was suctioned out. A total volume of 15 to 20 ml of precipitated cells was collected. When a large amount of matrix components was contained, the matrix components were filtered out using a 100-μm filter. Thereafter, centrifugation was performed as required.

5) 15 ml of Ficoll (registered trademark) was added to a 50-ml tube. Thereafter, 15 to 20 ml of the cell solution was added very slowly to form a layer thereon.

6) The tube was centrifuged at 400×g for 30 minutes (18 to 20° C.).

7) After centrifugation, the cell solution was separated into four layers: from above, A layer (cell-free layer, transparent); B layer (mononuclear cell layer, pale red color); C layer (Ficoll layer, transparent); and D layer (erythrocyte layer, deep red). Adhesion cells including stem cells were contained in the B and C layers. The A layer was suctioned off. The B layer and the C layer (about 3 ml) were recovered as a cell suspension, which in turn was transferred to a 50-ml tube.

8) Serum-supplemented PBS (PBS supplemented with 10% FBS or 10% human serum) was added to the recovered cell suspension to a volume of 50 ml. The mixture was mixed by pipetting, followed by centrifugation (400×g, 5 minutes).

9) The supernatant was suctioned off. Serum-supplemented PBS was added again to a volume of 50 ml. The mixture was mixed by pipetting, followed by centrifugation (400×g, 5 minutes).

10) The supernatant was sectioned off. The precipitated cells containing stem cells were recovered.

(II) Preparation Method 2

1) A liquid portion of an aspirate from liposuction was suctioned using a suction tube within a clean bench and was passed through a reservoir with a filter (pore size: 120 μm). The resultant filtrate was enclosed in a closed separation bag.

2) Centrifugation was performed three times using a cell separator (a blood component separating device: ASTEC204 available from AMCO, Inc., Tokyo, Japan) to remove platelets having smaller specific gravity, erythrocytes having larger specific gravity, and granulocytes as much as possible.

3) A fraction (about 30 to 40 ml) containing a high concentration of stem cells was collected. The specific gravity of the isolated cells was within the range of 1.050 to 1.075.

The specific gravity of a cell can be roughly determined as follows. A density gradient centrifugation medium, such as Percoll™, RediGrad™, or the like, was formulated in sodium chloride solution or sucrose solution. Collected cells and density marker beads are added to the mixture, followed by centrifugation. The mixture is separated into 5 to 10 layers, depending on the beads). The layer which contains a cell shows the specific gravity of the cell.

FIG. 1 shows a photograph of the isolated cells.

Example 3

Characterization of Recovered Stem Cells

The stem cells recovered in Example 2 were characterized by the following procedure using FACS.

About 5 ml of cell suspension was washed twice with staining medium (SM; PBS supplemented with 0.5% bovine serum albumin and 0.05% $NaN_3$). The cells were counted as required.

Labeled antibodies (label(s): phycoerythrin (PE), allophycocyannin (APC), and/or fluorescein isothiocyanate (FITC)) was added to about 1 to $10 \times 10^6$ cells/ml cell suspension to a final concentration of 0.001 to 0.1 μg/ml.

The mixture was incubated on ice for 30 minutes, followed by washing the cells. The concentration of the cell floating solution was adjusted with SM to about $5 \times 10^5$ cells/ml.

FACS Vantage (Becton Dickinson) was used. The label of the antibody was used as a marker to analyze the expression of each CD protein in isolated stem cells. As a result, it was revealed that stem cells, which were derived from a liquid portion of an aspirate from liposuction, expressed CD90 and CD49d as shown in Table 1.

The isolated stem cell was subcultured twice in DMEM. Subculture was conducted at 80% confluence. After the second subculture, the cell was analyzed by FACS as described above. The results are shown in Table 1.

TABLE 1

(Expression of various CDs in stem cells after twice subculture procedures)

| CD | Expression level |
|---|---|
| 3 | − |
| 4 | − |
| 11c | − |
| 13 | ++ |
| 14 | − |
| 15 | − |
| 16 | − |
| 19 | − |
| 29 | ++ |
| 31 | + |
| 33 | − |
| 34 | + |
| 36 | ++ |
| 38 | − |
| 44 | + |
| 45 | + |
| 49d | ++ |
| 54 | + |
| 56 | − |
| 58 | + |
| 61 | − |
| 62E | − |
| 62P | − |
| 69 | − |
| 71 | ++ |
| 73 | ++ |
| 90 | ++ |
| 104 | − |
| 105 | ++ |
| 106 | − |
| 117 | + |
| 135 | − |
| 144 | − |
| 146 | + |
| 151 | ++ |
| 235a | − |
| SH3 | + |
| STRO-1 | + |

"−" = no detection of expression,
"+" = detection in 20% or less of cells, and
"++" = detection in 20% or more of cells.

According to the above-described results, although the stem cells prepared from the liquid portion of an aspirate from liposuction included cell populations corresponding to mesenchymal stem cells, the stem cells included CD31, 34-positive cells, which are not included in fat-derived stem cells prepared by conventional techniques. Therefore, it can be understood that stem cells prepared by the method of the present invention can be easily and efficiently differentiated into vascular endothelium (vascularization). In addition, CD expression, which was used herein as a marker, was confirmed after two subculture procedures. Therefore, it is understood that the stem cell of the present invention does not substantially change the phenotype after about two subculture procedures.

Example 4

Characterization of Stem Cells Recovered from Liquid Portion of Aspirate from Liposuction Obtained from a Plurality of Subjects Further, stem cells were recovered from liquid portions of aspirates from liposuction obtained from a plurality of subjects, followed by characterization. The results are shown below.

TABLE 2

(Results of characterization of stem cells recovered from liquid portions of aspirates from liposuction obtained from a plurality of subjects)

| Subject | A | B | C |
|---|---|---|---|
| Passage | 7 | 1 | 1 |
| Number of cells | 10,000 | 10,000 | 30,000 |
| Medium | DMEM | M199 | M199 |
| CD4 | − | 5.1 | N.T. |
| CD13 | + | 100.0 | 99.6 |
| CD16 | N.T. | 1.9 | 1.1 |
| CD29 | + | 99.9 | 98.9 |
| CD31 | − | 8.0 | 1.7 |
| CD34 | − | 80.3 | 80.6 |
| CD36 | + | 27.6 | 15.6 |
| CD44 | + | 100.0 | 99.4 |
| CD45 | − | 8.1 | 0.9 |
| CD49d | + | 78.0 | 79.4 |
| CD54 | N.T. | N.T. | 95.6 |
| CD56 | N.T. | 2.1 | 9.0 |
| CD57 | N.T. | N.T. | 0.1 |
| CD69 | − | 0.0 | 0.0 |
| CD71 | + | 95.4 | 53.5 |
| CD73 | N.T. | 89.5 | 98.5 |
| CD90 | + | 100.0 | N.T. |
| CD105 | + | 99.8 | 92.4 |
| CD106 | − | 0.6 | 1.2 |
| CD117 | − | 10.4 | 7.1 |
| CD135 | − | 0.5 | 0.0 |
| CD151 | + | 98.7 | 99.4 |
| CD235a | − | 4.5 | N.T. |
| STRO-1 | N.T. | 4.1 | 5.7 |

Numerals show the proportion (%) of stem cells, which expressed each protein, in a group of cells, "−" = no expression detected, "+" = expression detected, and N.T. = no test.

Most of the collected stem cells were positive to CD13, CD29, CD34, CD36, CD44, CD49d, CD54, CD58, CD71, CD73, CD90, CD105, CD106, CD151, and SH3. Therefore, the adipose-derived precursor cell of the present invention is a cell which expresses at least one protein selected from the group consisting of CD13, CD29, CD34, CD36, CD44, CD49d, CD54, CD58, CD71, CD73, CD90, CD105, CD106, CD151, and SH3. A stem cell expressing CD106 is a feature of the adipose-derived precursor cell used in the present invention. A portion of the stem cell group was positive to CD31, CD45, CD117, and CD146, while another portion was negative.

The stem cell group was negative to CD3, CD4, CD14, CD15, CD16, CD19, CD33, CD38, CD56, CD61, CD62e, CD62p, CD69, CD104, CD135, and CD144. Therefore, the adipose-derived precursor cell of the present invention is a cell which does not express at least one of CD3, CD4, CD14, CD15, CD16, CD19, CD33, CD38, CD56, CD61, CD62e, CD62p, CD69, CD104, CD135, and CD144.

When the stem cell group was cultured in differentiation inducing medium, the expression of proteins specific to an organ, such as bone, cartilage, fat, or the like, was recognized after 2 to 3 weeks. The stem cell group did not express CD56, which is expressed by most fibroblasts, as is different from human dermis-derived cultured fibroblasts. In contrast, the expression of CD105 exhibited by the stem cell group was not usually observed in fibroblasts. The expression of CD49d exhibited by the stem cell group was not typically observed in bone marrow-derived mesenchymal stem cells.

In addition, for CD31, CD34, CD36, CD45, CD106, and CD117, the expression tended to disappear when the period of culture was long. Therefore, if subculture is continued, the expression of CD106 observed before subculture may not be observed.

Example 5

Preparation of Fat Tissue

Next, as differentiated cells, fat tissue was prepared from human subjects who had given their informed consent. Separation was conducted with techniques well known in the art. Briefly, human fat tissue was aseptically separated from fat tissue suctioned from human subjects who had given their informed consent. The tissue mass was preserved in medium for adipocytes ((500 ml) composition=Eagle's medium 4.75 g; 10% NaHCO$_3$ 10 ml; glutamine 0.3 g; kanamycin (20 mg/ml) 1.5 ml; penicillin streptomycin 5 ml; FBS (10%)). The tissue mass may be used as it is or may be separated into adipocytes, which are in turn used.

| Ingredients of Eagle's medium (per 9.5 g) | |
|---|---|
| sodium chloride | 6400 mg |
| potassium chloride | 400 mg |
| calcium chloride (anhydride) | 200 mg |
| magnesium sulfate (anyhdride) | 97.7 mg |
| sodium dihydrogen phosphate (anhydride) | 108 mg |
| mercuric nitrate (nonahydrate) | 0.1 mg |
| grape sugar | 1000 mg |
| sodium pyruvate | 110 mg |
| succinic acid | 106 mg |
| sodium succinate (hexahydrate) | 27 mg |
| L-arginine hydrochloride | 84 mg |
| L-cysteine hydrochloride (monohydrate) | 70.3 mg |
| glycine | 30 mg |
| L-histidine hydrochloride (monohydrate) | 42 mg |
| L-isoleucine | 104.8 mg |
| L-leucine | 104.8 mg |
| L-lysine hydrochloride | 146.2 mg |
| L-methionine | 30 mg |
| L-phenylalanine | 66 mg |
| L-serine | 42 mg |
| L-threonine | 95.2 mg |
| L-tryptophan | 16 mg |
| L-disodium tyrosine | 89.5 mg |
| L-valine | 93.6 mg |
| choline bitartrate | 7.2 mg |
| folic acid | 4 mg |
| nicotinamide | 4 mg |
| calcium pantothenate | 4 mg |
| pyridoxal hydrochloride | 4 mg |
| riboflavin | 0.4 mg |
| thiamine hydrochloride | 4 mg |
| i-inositol | 7.2 mg |
| phenol red | 5 mg |

Example 6

Mixture of Adipocyte

Next, the adipose-derived precursor cell (PLA) prepared in Example 1 was not subject to further treatment and was mixed with the fat tissue (adipocyte group), which had been prepared as differentiated cells in Example 2. It was determined whether or not the differentiation was promoted to cause regeneration.

1 ml (900 mg) of fat tissue mass (A), which had been prepared in Example 2, or a mixture (B) of 1 ml (900 mg) of the fat tissue with 10 ml of suctioned fat-derived PLA prepared in Example 1 was subcutaneously injected to the dorsal portion of SCID mice (Charles River Japan). Injection was performed with a syringe. After 4 weeks, tissue was collected from the injection site. The weight of the implanted fat tissue was determined and the tissue was analyzed.

Figure 2:
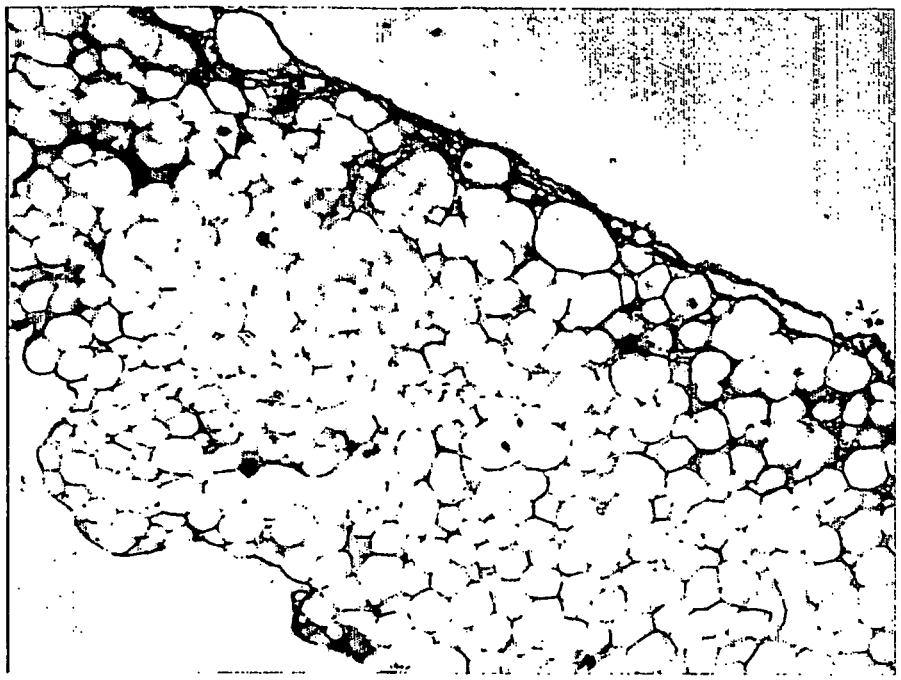
FIG. 2 is a photograph showing a section of fat tissue (×40).
Figure 3:
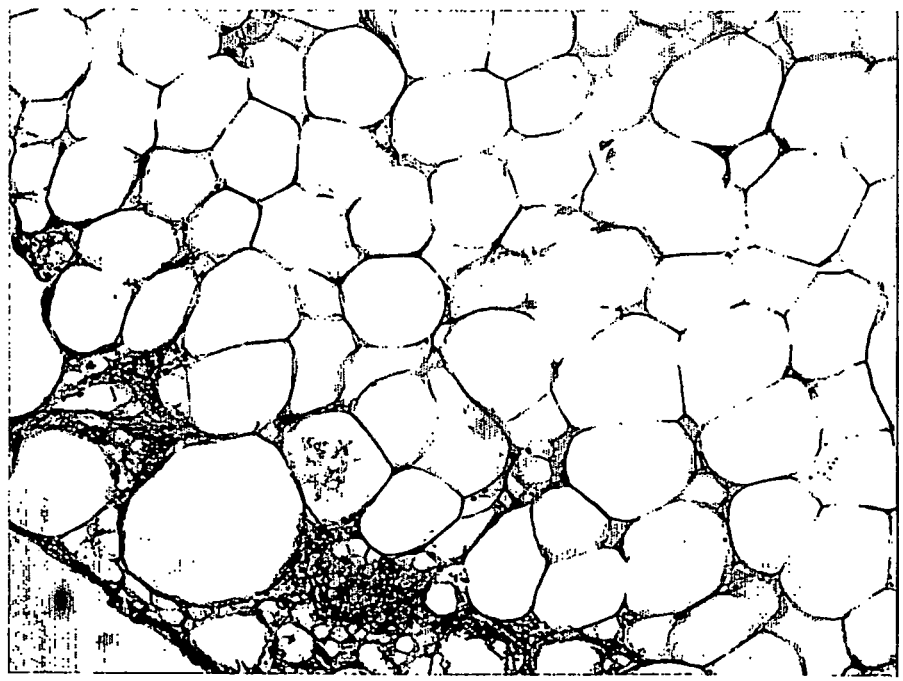
FIG. 3 is another photograph showing a section of fat tissue (×1000).
Figure 4:
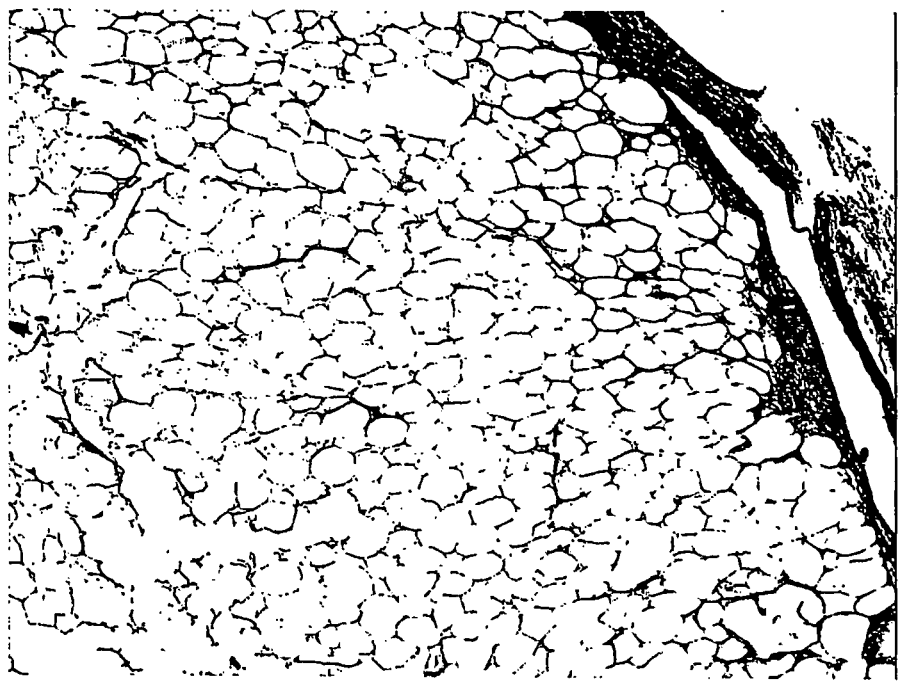
FIG. 4 is a photograph showing a section of fat tissue to which adipose-derived precursor cells were added (×40).
Figure 5:
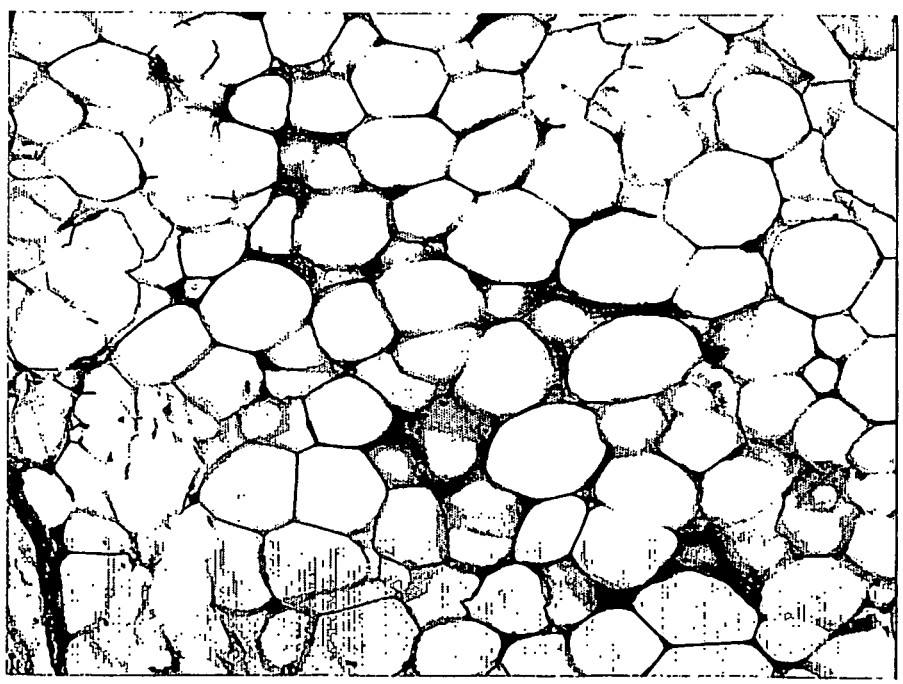
FIG. 5 is another photograph showing a section of fat tissue to which adipose-derived precursor cells were added (×100).

FIGS. 2 and 3 are photographs showing sections of the tissue collected 4 weeks after implantation in the case of (A) (two samples). FIGS. 4 and 5 are photographs showing sections of the tissue collected 4 weeks after implantation in the case of (B) (two samples). As can be seen, the influence of blended PLA on the maintenance of the weight of the tissue was revealed.

(Regeneration of Fat Tissue by Mixture of Adipocyte)

Figure 6:
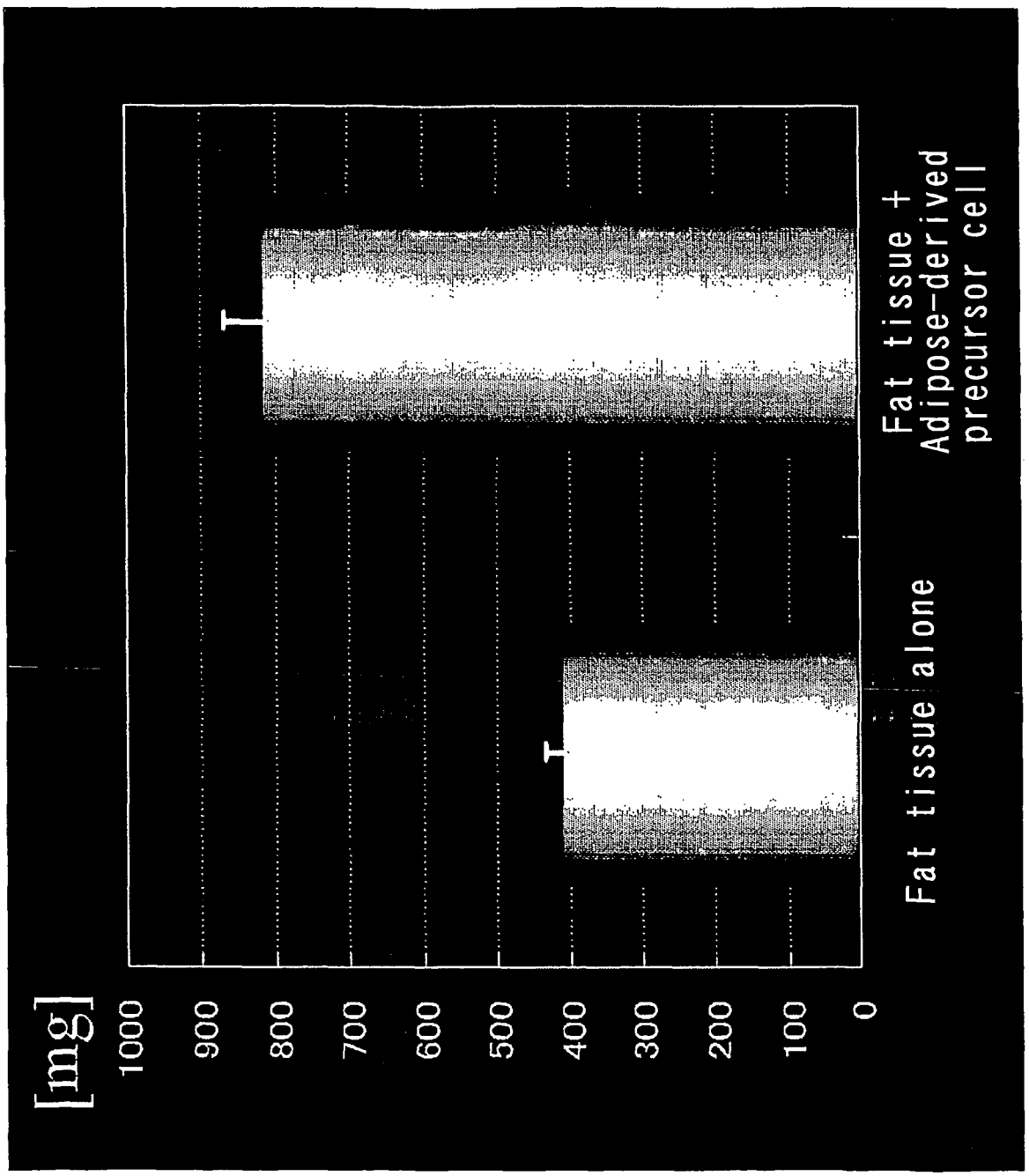
FIG. 6 is a graph showing an influence of adipose-derived precursor cells on the regeneration of fat tissue. The left portion indicates the case where only fat tissue was implanted (weight 4 weeks after implantation is shown), while the right portion indicates the case where fat tissue was implanted along with adipose-derived precursor cells (weight 4 weeks after implantation is shown).
Figure 7:
FIG. 7 shows the incision of an SCID (severe combined immunodeficiency) mouse 4 weeks after implantation in Example 3.
Figure 8:
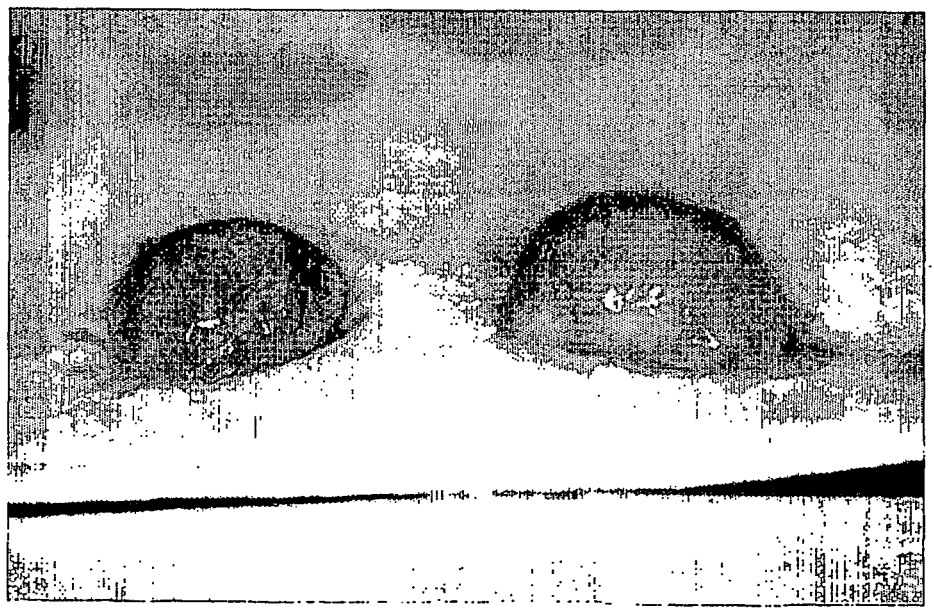
FIG. 8 shows fat tissue extracted form a SCID mouse in Example 3.

When PLA and fat tissue were mixed, the average weight of regenerated fat was 814 mg (n=8). When only fat tissue was used, the average weight was 408 mg (n=5). Thus, the influence of PLA was clearly demonstrated (p<0.001) (FIG. 6). FIG. 7 shows incision of the SCID mouse 4 weeks after implantation. FIG. 8 shows fat tissue removed from the SCID mouse. FIGS. 7 and 8 each show only fat tissue. The right-hand portion indicates the tissue when the mixture containing PLA was administered. As can be seen from FIGS. 7 and 8, the tissue was significantly bigger when the mixture containing PLA was administered.

When only fat tissue was injected, the weight of the fat tissue was reduced to about half after 4 weeks. This may be because the fat tissue underwent necrosis. The reason the weight of the tissue was maintained when the mixture containing PLA was administered, is considered to be that PLA was induced to differentiate into fat tissue, or PLA had a function to prevent disruption of tissue, or both.

Example 7

Effect of PLA which was Maintained and Cultured in DMEM

The PLA prepared in Example 1 was maintained in DMEM (the same as used in Example 3). The resultant PLA was used to confirm a similar effect. Specifically, this preparation was used instead of the adipose-derived precursor cell (PLA) prepared in Example 1 and used in Example 3. As a result, when 250 million of the PLAs were added to 900 mg of fat, about 40 to 50% of the fat tissue successfully grew. Therefore, it was found that stem cells, which are collected and maintained in growth culture, can be used.

Example 8

Effect of PLA Cultured in P199

Adipose-derived precursor cells cultured in M-199 were used instead of the adipose-derived precursor cell (PLA) prepared in Example 1 and used in Example 3. M-199 contained the following ingredients.

| Ingredients of M-199 (medium for vascular endothelial cells) (per liter): | |
|---|---|
| Medium 199 | 9.5 g |
| NaHCO$_3$ | 2.2 g |
| FBS | (15%) |
| acidic-FGF | 2 µg |

-continued

Ingredients of M-199 (medium for vascular
endothelial cells) (per liter):

| heparin | 5 mg |
| --- | --- |
| antibiotic-antimycotic | 10 ml |
| (Note) the unit of ingredients below is mg/ml | |
| L-alanine | 50 |
| L-arginine•HCl | 70 |
| L-aspartic acid | 60 |
| L-cysteine | 0.1 |
| L-cystine | 20 |
| L-glutamic acid | 150 ($H_2O$) |
| L-glutamine | 100 |
| glycine | 50 |
| L-histidine•HCl•$H_2O$ | 20 |
| hydroxy-L-proline | 10 |
| L-isoleucine | 40 |
| L-leucine | 120 |
| L-lysine•HCl | 70 |
| L-methionine | 30 |
| L-phenylalanine | 50 |
| L-proline | 40 |
| L-serine | 50 |
| L-threonine | 60 |
| L-tryptophan | 20 |
| L-tyrosine | 40 |
| L-valine | 50 |
| glutathione (reduced form) | 0.05 |
| $CaCl_2$•$2H_2O$ | 264.9 |
| KCl | 400 |
| $MgSO_4$•$7H_2O$ | 97.7 (anhydride form) |
| NaCl | 6800 |
| $NaHCO_3$ | 2200 |
| $NaH_2PO_4$ | 140 ($2H_2O$) |
| $Fe(NO_3)_3$•$9H_2O$ | 0.72 |
| $CH_3COONa$•$3H_2O$ | 83 |
| phenol red | 15 |
| D-biotin | 0.01 |
| folic acid | 0.01 |
| nicotinamide | 0.025 |
| calcium pantothenate | 0.01 |
| pyridoxal•HCl | 0.025 |
| pyridoxine•HCl | 0.025 |
| riboflavin | 0.01 |
| thiamine•HCl | 0.01 |
| adenine | 10 ($SO_4$) |
| choline chloride | 0.5 |
| hypoxanthine | 0.3 |
| i-inositol | 0.05 |
| p-aminobenzoic acid | 0.05 |
| guanine•HCl | 0.3 |
| xanthine | 0.3 |
| thymine | 0.3 |
| uracil | 0.3 |
| nicotinic acid | 0.025 |
| vitamin A | 0.1 |
| calciferol | 0.1 |
| menadione | 0.01 |
| α-tocopherol | 0.05 |
| ascorbic acid | 20 |
| Tween 80 | 20 |
| cholesterol | 0.2 |
| ATP•2Na | 1 |
| adenylic acid | 0.2 |
| ribose | 0.5 |
| deoxyribose | 0.5 |

As a result, it was found that when adipose-derived precursor cells cultured in M-199 medium are added to fat, fat tissue undergoes growth. Therefore, it was found that stem cells which are maintained in any medium after collection can be used.

Example 9

Application of Bone Cells

Next, bone cells are used to conduct a similar experiment of implanting the cell mixture of the present invention. For bone cells, bones (bone tissue) are collected from mice with techniques well known in the art The bone tissue is mixed with PLA prepared in Example 1, and the mixture is implanted into a bone. In this case, it is observed that the regeneration of the bone is supported by the mixture implant of the present invention.

Example 10

Application to Vascularization

Next, blood vessel cells are used to conduct a similar experiment of implanting the cell mixture of the present invention. For blood vessel cells, blood vessels (blood vessel tissue) are collected from mice with techniques well known in the art. The blood vessel tissue is mixed with PLA prepared in Example 1, and the mixture is implanted into a blood vessel. In this case, it is observed that the regeneration of the blood vessel is supported by the mixture implant of the present invention.

Example 11

In vivo Effect

Next, the cell mixture of the present invention was implanted into a human patient who wished to enhance the volume of her breast so as to determine whether or not the desired effect was actually obtained.

The subject was a 37 year old woman (chest circumference, other references for evaluation of breast (e.g., the AAA cup, etc.).

1,300 ml of fat was suctioned from the female patient. From the aspirate, 600 ml of fat, a liquid used to wash the fat, and stem cells were prepared. In washing the fat, saline solution (0.9% NaCl) was used. Specifically, the fat was prepared as follows.

1) The female subject was systemically anesthetized and Tumescent (1,000 ml of saline, 1 mg of adrenaline) was injected into a site from which fat was to be suctioned.

2) Fat was suctioned off using SAL PUMP (SAL 76-A, Keisei Ika-Kogyo, Tokyo, Japan).

3) Suctioned tissue was washed using saline (0.9% NaCl, Ohtsuka Pharmaceuticals, Co., Ltd.). The resultant liquid and suctioned fat after washing were separated.

4) Cells were collected from the entire liquid and a part (600 ml) of the suctioned fat after washing in accordance with the procedure described in Example 1.

About $3.7 \times 10^8$ cells could be obtained from 600 ml of fat. These cells included stem cells and other cells, and the stem cells were concentrated as compared to naturally-occurring fat tissue. About $8.2 \times 10^8$ cells could be obtained from the liquid. The stem cells were prepared with the procedure described in Example 1.

From the remainder 700 ml, 660 ml of the suctioned fat was used in operation. The suctioned fat was injected to the right and left breasts (a half (330 ml) thereof for each). For injection, a 10-cc LeVeen™ inflator (Boston Scientific Corp, MA) was used. Thereafter, the above-prepared stem cells were injected to the breasts. As the stem cell fraction, all of the above-prepared cells were used (among 1.19×10⁹ cells, it was estimated that the stem cells accounted for 5×10⁶ to 2×10⁷.

(Results)

Two months after operation, the chest circumstance was enhanced up to the B cup and the shape thereof was natural. In the case of conventional techniques in which only fat is injected, the shape is instable and often returns to the original shape over time. With the method of the present invention, a satisfactory level of affinity and natural shape can be obtained. Thus, a significant effect of cosmetic improvement is obtained. In conventional breast augmentation surgery, silicone or fat is used as it is. However, the breasts are often deformed as the skin is shrunk due to aging or silicone or fat is often absorbed into the body so that the effect thereof is reduced. In the method of the present invention, the affinity was increased by 20 to 50% or more as compared to when fat is used alone. Thus, the present invention provides an epoch-making useful method in the field of cosmesis, orthopedics, plastic surgery, and the like.

The above-described methods were similarly applied to another patient. As a result, a significant effect was observed in terms of shape, stability, affinity, and the like. Some of the patients had not been satisfied with conventional silicone and/or fat-only implantation.

In addition, in the method of the present invention, fat was removed from a portion unwanted by the patient, so that the patient was mentally satisfied. Therefore, such an effect, which cannot be conventionally obtained, could be achieved.

Although certain preferred embodiments have been described herein, it is not intended that such embodiments be construed as limitations on the scope of the invention except as set forth in the appended claims. All patents, published patent applications and publications cited herein are incorporated by reference as if set forth fully herein.

INDUSTRIAL APPLICABILITY

The present invention demonstrated that adipose-derived precursor cells obtained by a simple technique can be applied to regenerative medicine. Therefore, the present invention is applicable to medical industries.

The invention claimed is:

1. A method for an in vitro preparation of an adipocyte culture used for treatment or improvement of a cosmetic condition, comprising the steps of:
   A) obtaining a cell mixture from a fat portion or a liquid portion of aspirates comprising adipose-derived precursor cells and adipocytes;
   B) culturing the cell mixture under sufficient conditions in the presence of at least one differentiation promoting agent to produce the adipocyte culture having adipocytes in a ratio (a):(b) from about 1:1 to 5:1, the ratio being at least 2 to 10 times the in vivo ratio of (a):(b) in fat tissue.
   wherein the cosmetic condition is breast augmentation or tissue augmentation.

2. The method according to claim 1, wherein the adipose-derived precursor cell is a cell expressing at least one protein selected from the group consisting of CD13, CD29, CD34, CD36, CD44, CD49d, CD54, CD58, CD69, CD71, CD73, CD90, CD105, CD106, CD151, and SH3.

3. The method according to claim 2, wherein the adipose-derived precursor cell is a cell expressing CD13, CD29, CD34, CD36, CD44, CD49d, CD54, CD58, CD69, CD71, CD73, CD90, CD105, CD106, CD151, and SH3.

4. The method according to claim 2, wherein the adipose-derived precursor cell is the cell further expressing at least one protein selected from the group consisting of CD31, CD45, CD117, and CD146.

5. The method according to claim 1, wherein the adipose-derived precursor cell is a cell not expressing CD56.

6. The method according to claim 1, wherein the adipose-derived precursor cell is a cell expressing CD49d but not CD56.

7. The method according to claim 1, wherein the agent is selected from the group consisting of adrenocortical steroids, insulin, glucose, indomethacin, isobutyl-methylxanthine (IBMX), ascorbic acid and a derivative thereof, glycerophosphate, estrogen and a derivative thereof, progesterone and a derivative thereof, androgen and a derivative thereof, growth factors, pituitary gland extracts, pineal body extracts, retinoic acid, vitamin D, thyroid hormone, fetal bovine serum, equine serum, human serum, heparin, sodium hydrogen carbonate, HEPES, albumin, transferrin, selenates, linoleic acid, 3-isobutyl-1-methylxanthine, demethylating agent, histone deacetylating agents, activin, cytokine, hexamethylenebisacetamide (HMBA), dimethylacetamide (DMA), dibutyl cAMP (dbcAMP), dimethylsulfoxide (DMSO), iododeoxyuridine (IdU), hyroxyurea (HU), cytosine arabinoside (AraC), mitomycin C (MMC), sodiumbutyrate (NaBu), polybrene, and selenium.

8. The method of claim 1, wherein the cosmetic condition is breast augmentation.

* * * * *